(12) United States Patent
Allen et al.

(10) Patent No.: US 8,642,528 B2
(45) Date of Patent: Feb. 4, 2014

(54) ALKYL LACTYLLACTATES AND PROCESSES OF MAKING THE SAME

(75) Inventors: David R Allen, Chicago, IL (US); Anatoliy A. Dameshek, Indian Creek, IL (US); Branko Sajic, Lincolnwood, IL (US); Irene Shapiro, Buffalo Grove, IL (US); Xue Min Dong, Lincolnshire, IL (US); Christopher D Smith, Watkinsville, GA (US); Jacqueline M Pytel, Libertyville, IL (US); Jeremy Weitgenant, Grayslake, IL (US)

(73) Assignee: Stepan Company, Northfield, IL (US)

( * ) Notice: Subject to any disclaimer, the term of this patent is extended or adjusted under 35 U.S.C. 154(b) by 699 days.

(21) Appl. No.: 12/349,316

(22) Filed: Jan. 6, 2009

(65) Prior Publication Data

US 2009/0200511 A1    Aug. 13, 2009

Related U.S. Application Data

(63) Continuation of application No. PCT/US2007/072975, filed on Jul. 6, 2007.

(60) Provisional application No. 60/819,145, filed on Jul. 6, 2006, provisional application No. 60/842,476, filed on Sep. 6, 2006, provisional application No. 60/896,205, filed on Mar. 21, 2007.

(51) Int. Cl.
   *C11D 17/00* (2006.01)

(52) U.S. Cl.
   USPC ............ 510/434; 510/340; 510/405; 252/364

(58) Field of Classification Search
   USPC .......... 252/182.12, 364; 560/1, 180; 510/340, 510/405, 434
   See application file for complete search history.

(56) References Cited

U.S. PATENT DOCUMENTS

| | | | |
|---|---|---|---|
| 2,350,388 A | 6/1944 | Claborn | |
| 2,371,281 A | 3/1945 | Claborn | |
| 3,144,341 A | 8/1964 | Thompson et al. | |
| 3,294,837 A | 12/1966 | Thompson | |
| 3,929,678 A | 12/1975 | Laughlin et al. | |
| 4,199,483 A | 4/1980 | Jones | |
| 4,222,905 A | 9/1980 | Cockrell, Jr. | |
| 4,295,217 A | 10/1981 | Fennel, Jr. et al. | |
| 5,399,353 A * | 3/1995 | Bartnik et al. | ................. 424/438 |
| 5,618,850 A | 4/1997 | Coury et al. | |
| 5,705,147 A | 1/1998 | Shapiro et al. | |
| 6,297,350 B1 | 10/2001 | Kricheldorf et al. | |
| 6,448,214 B1 | 9/2002 | Del Duca et al. | |
| 6,630,569 B1 | 10/2003 | Jeschke et al. | |
| 2005/0215453 A1 | 9/2005 | Teissier | |
| 2008/0287538 A1* | 11/2008 | Scholz et al. | ................. 514/552 |

FOREIGN PATENT DOCUMENTS

CA      2283517 A1 *  10/1998

OTHER PUBLICATIONS

European Search Report corresponding to European Patent Application Serial No. 07812688.5-1211, dated Jul. 6, 2009.
Anon, "Alkyl lactyllactates and preparation and applications thereof." ip.com Journal, Mar. 22, 2007, XP002533919.
Rehberg et al., "Esters of Lactyllactic Acid." Journal of American Chemical Society, vol. 74, Mar. 20, 1952. XP001113148.
Kumar et al., "Poly(3-hydroxybutyrate)-depolymerase from Pseudomonas lemoignei: Catalysis of Esterifications in Organic Media." Journal of Organic Chemistry, vol. 65, No. 23, 2000. XP002533920.
Office Action in U.S. Appl. No. 12/349,329 dated Sep. 15, 2009.
Office Action in U.S. Appl. No. 12/349,329 dated Apr. 29, 2010.
Office Action in U.S. Appl. No. 12/349,239, dated Oct. 13, 2010.

* cited by examiner

*Primary Examiner* — Mark Kopec
*Assistant Examiner* — Haidung Nguyen
(74) *Attorney, Agent, or Firm* — McAndrews, Held & Malloy, Ltd.

(57) ABSTRACT

Provided are alkyl lactyllactate compositions that can be prepared from (1) lactide or alternatively lactic acid, and (2) a hydroxyl containing compound such as an alcohol, preferably a fatty alcohol or an alkoxylated alcohol, with (3) an acid catalyst. Preferably, the fatty alcohol contains from about 6 to 18 carbon atoms, such as lauryl alcohol. The alkyl lactyllactates can be used as surfactants, emulsifiers, skin feel agents, film formers, thickeners, rheological modifiers, etc., for personal care and other application areas. Compositions containing at least one alkyl lactyllactate are also provided. The compositions can further contain at least one surfactant.

15 Claims, 22 Drawing Sheets

Figure 7
Stability Results

| System | Time (wks) | Room Temperature | | 50° C | |
|---|---|---|---|---|---|
| | | pH | Viscosity (cps) | pH | Viscosity (cps) |
| Non-buffered | 0 | 6.0 | 4,200 | 6.0 | 4,200 |
| Buffered | 0 | 5.6 | 600 | 5.6 | 600 |
| Non-buffered | 1 | | | | |
| Buffered | 1 | 5.4 | 600 | 5.1 | 700 |
| Non-buffered | 2 | 6.0 | 4,000 | 4.0 | 3,000 |
| Buffered | 2 | 5.3 | 600 | 4.9 | 700 |
| Non-buffered | 3 | | | | |
| Buffered | 3 | 5.3 | 600 | 4.8 | 800 |
| Non-buffered | 4 | | | | |
| Buffered | 4 | 5.4 | 550 | 4.6 | 700 |

Viscosity v. NaCl% Results

Expert Panel Hand Foaming Results

Note: Foaming results represent average of five expert panelists; a difference equal to or greater than 10 mL is considered significant (higher score = better).

Note: Foaming results represent average of five expert panelists; a difference equal to or greater than 10 mL is considered significant (higher score = better).

Properties

Note: Higher score = better performance; a difference equal to or greater than 1 is considered significant with scores rated 1-5.

Note: a difference equal to or greater than 0.75 is considered to be significant on a scale of 1-5; the higher the score, the better performance Hand Washing Foaming Result for L3, Amphoacetate, and Sulfsuccinate as Ternary Surfactants in CS-230/HCG system Viscosity v. NaCl% Results

ALKYL LACTYLLACTATES AND PROCESSES OF MAKING THE SAME

RELATED APPLICATIONS

This application is a continuation of International Application Serial No. PCT/US2007/072975 (International Publication No. WO 2008/006076A3), having an International filing date of Jul. 6, 2007. This PCT application claims priority to U.S. provisional patent application Ser. No. 60/819,145, filed Jul. 6, 2006, Ser. No. 60/842,476, filed Sep. 6, 2006, and Ser. No. 60/896,205, filed Mar. 21, 2007. The entire specifications of the PCT and provisional applications referred to above are hereby incorporated by reference. This application is related to a co-pending application Ser. No. 12/349,329 that is filed on the same date as this application.

FEDERALLY SPONSORED RESEARCH OR DEVELOPMENT

[Not Applicable]

BACKGROUND OF THE INVENTION

The presently described technology relates generally to alkyl lactyllactate compounds such as lauryl lactyllactate, and compositions comprising or incorporating such compounds. The presently described technology also relates generally to improved processes of making the alkyl lactyllactate compounds and derivatives thereof as well as compositions comprising or incorporating the same.

In the area of personal care, there is a desire for surfactants to be mild, salt-free and 100% active. Other desirable attributes include being in liquid form at room temperature, having a non-nitrogen containing structure, an ability to formulate in cold-mix applications, and an ability to perform as good as or better than existing surfactants.

For household, industrial and institutional cleaning products, both surfactants and solvents are important ingredients in these products. Desirable attributes for such products include the ability to emulsify, suspend or penetrate greasy or oily soils and suspend or disperse particulates, in order to clean surfaces; and then prevent the soils, grease, or particulates from re-depositing on the newly cleaned surfaces. For example, a laundry detergent product should desirably remove dirt from clothes and then keep the dirt in solution so that it is removed with the wash water instead of re-depositing on the washed clothes.

It is also desirable to have the ability to control the foaming of different household, industrial and institutional products depending on the desired end-use applications. For example, a liquid manual dish washing detergent preferably has the ability to foam in the presence of soil that is being removed from dishware. Yet, for a laundry detergent or dish washing detergent for use in a high efficiency washing machine, low foam is desired to achieve the best cleaning and to avoid excess foaming. Other desirable properties of such consumer products include the ability to clarify the formulation and to improve stability. For hard surface cleaners, it is desirable to have the ability to wet various surface types and couple or suspend soils to leave the surface free from residue in the form of streaking and/or filming.

It has been unexpectedly discovered that the alkyl lactyllactates of the present technology can meet one or more of the above desired attributes, among others. The alkyl lactyllactates can be incorporated into, for example, various compositions and used as surfactants, emulsifiers, skin feel agents, film formers, rheological modifiers, solvents, release agents, lubrication agents, conditioners, and dispersants, etc. Such compositions can be used in end-use applications including, but not limited to, personal care, as well as household and industrial and institutional cleaning products. They can also be used in oil field applications, gypsum foamers, paints and coatings, adhesives, or other applications requiring cold tolerance performance or winterization (e.g., applications requiring cold weather performance without the inclusion of additional volatile components).

U.S. Pat. Nos. 2,350,388 and 2,371,281 (Claborn) (the "Claborn patents") generally describe that an alkyl lactyllactate can allegedly be produced by heating a mixture of a dry lactide and an anhydrous alcohol at a temperature of from 70° to 90° C. for a period of about 6 to 8 hours in the presence of an acid catalyst and under anhydrous conditions. The Claborn patents also generally describe alkyl lactyllactates asserted to have properties desirable for solvents and plasticizers, and for production of other plasticizers.

However, the process to prepare alkyl lactyllactates as described in the Claborn patents requires a solvent to be used in the reaction mixture, which is either an excess amount of the alcohol or an inert organic liquid, such as benzene. The Claborn patents also require a reaction temperature of above 70° C. It is desirable, however, to eliminate the use of solvents in the reaction process for producing alkyl lactyllactates and/or to have a process that can run at a lower reaction temperature. Further, the Claborn patents do not appreciate the control and effect of chirality on the properties of the resultant alkyl lactyllactate. Nor do the Claborn patents teach how to make alkyl lactyllactates with different chiralities. Additionally, the Claborn patents do not appreciate the effects of the choice of alcohol (e.g., primary vs. secondary or tertiary; fatty alcohol vs. a lower alcohol) on the product yield, purity of the product, and properties of the product. Further, the Claborn patents do not appreciate and disclose alkyl lactyllactates that can be used as surfactants, emulsifiers, skin feel agents, film formers, thickeners, rheological modifiers, etc., for personal care and other application areas. Thus, it is desirable to have a process that can produce a better yield of a higher purity alkyl lactyllactate product without distillation or other purification. It is also desirable to make and use an alkyl lactyllactate with a selected chirality to achieve or improve certain desired end-product properties.

U.S. Pat. No. 3,144,341 (Thompson) (the "Thompson patent") discloses stearyl lactyllactate and cetyl lactyllactate produced by reacting stearyl alcohol or cetyl alcohol with lactic acid (2-hydroxypropionic acid, $CH_3CHOHCOOH$). The stearyl lactyllactate and cetyl lactyllactate so produced are generally described as emulsifying agents particularly suitable as shortening agents in cake mixes and the like. The Thompson patent states that the reaction product is a mixture of stearyl lactyllactate and stearyl lactate, which are referred to as stearyl lactoyl lactate and stearyl lactate, respectively. Col. 3, lines 29-31. The Thompson patent further asserts that stearyl lactate is less effective than the desired stearyl lactyllactate. Col. 3, lines 56-57. The reference recommends using 2.1 moles of lactic acid per one mole of stearyl alcohol (or cetyl alcohol), col. 1, lines 31-54, but suggests that the reaction of stearyl lactyllactate with an additional mole of lactic acid offered no appreciable advantages. Col. 3, lines 57-59. The Thompson patent also does not teach or suggest the use of a catalyst for the reaction of the alcohol with lactic acid. Because it is believed that alkyl lactyllactates are more efficient, and can provide better performance and stability than alkyl lactates, it is desirable to have an improved process that can produce an alkyl lactyllactate product via a lactic acid route that contains a higher ratio of the lactyllactate component over the lactate component.

BRIEF SUMMARY OF THE INVENTION

In one aspect, the presently described technology provides an alkyl lactyllactate of the following general structure:

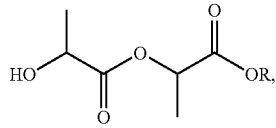

wherein R is an alkyl group or alkoxylated alkyl group. R can be derived from a hydroxyl containing compound such as an alcohol, preferably, a primary alcohol.

Preferably, the alkyl lactyllactates of the present technology exhibit a specific chirality, which can be, for example, L-lactyllactate, D-lactyllactate, an L,D/D,L racemic lactyllactate made from, for example, meso-lactide, or an L,L/D,D racemic lactyllactate made from, for example, racemic lactide, or a mixture thereof. One preferred alcohol is a fatty alcohol, such as those containing from about 6 to about 18 carbon atoms.

In accordance with some embodiments, preferably, at least one alkyl lactyllactate of the present technology is an L-alkyl lactyllactate having the following general structure:

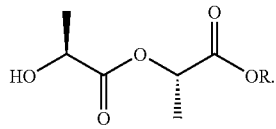

In accordance with some other embodiments, preferably, one or more of the alkyl lactyllactates is an L,D/D,L racemic lactyllactate made from a meso-lactide, or a mixture of lactyllactates made from a mixture of L-lactide and meso-lactide.

In accordance with some embodiments, at least one alkyl lactyllactate of the present technology can be represented by the following general structure:

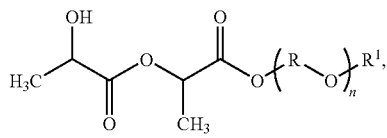

wherein, R contains about two to about six, alternatively about two to about four, preferably about two to about three carbon atoms, $R^1$ contains about one to about twenty-two, alternatively about one to about eighteen, alternatively about six to about eighteen, alternatively about twelve to about fourteen, alternatively about one to about six carbon atoms (e.g., four carbon atoms), and the number of repeat units (n) can vary from about 0 to about 100. When n is 0, the alkyl group in the lactyllactate is not alkoxylated. When n is not 0, the alkyl lactyllactates contain at least one alkoxylate group. For personal care, home care or other cleansing applications, n is preferably from about one to about twelve, alternatively from about one to about nine, alternatively from about one to about six, alternatively from about two to about four.

Preferably, the hydroxyl containing compound used to make the alkyl lactyllactate of the presently described technology contains at least one primary hydroxyl group (OH). When the hydroxyl containing compound contains two or more primary hydroxyl groups (OH's), a compound containing two or more lactyllactate groups can be formed. For example, when a compound containing two primary hydroxyl groups (e.g., glycerin or ethoxylated glycerin) is used as the bridging molecule, the alkyl lactyllactate, in accordance with some embodiments of the present technology, can be represented by the following general structure:

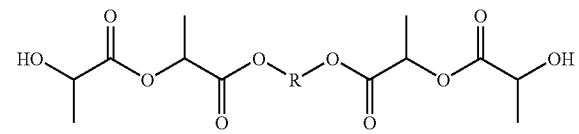

In accordance with some embodiments, the R group in the above formula preferably contains from about two to about twenty four, more preferably from about two to about eight carbon atoms. For example, the R group can be derived from glycerin or alkoxylated glycerin.

In another aspect, the presently described technology provides one or more processes for producing an alkyl lactyllactate. At least one process includes, for example, the steps of: providing at least one mixture comprising at least one lactide, at least one hydroxyl containing compound (e.g., a fatty alcohol or an alkoxylated alcohol), and at least one acid catalyst; and reacting the lactide and the hydroxyl containing compound at room temperature or an elevated temperature. The lactide and the hydroxyl containing compound can be used in equivalent molar amounts. The reaction temperature can be within the range of from about 15° C. to about 150° C., preferably from about 20° C. to about 100° C., more preferably from about 30° C. to about 70° C., and most preferably from about 40° C. to about 60° C. The acid catalyst can be, for example, $H_2SO_4$, HCl, p-toluenesulfonic acid (pTSA), or a NAFION® ionomer (a sulfonated tetrafluoroethylene copolymer, CAS No. 31175-20-9, available from E.I. du Pont de Nemours and Company), or a mixture thereof. The lactide used can be in a solid or liquid form, and can be L-lactide, D-lactide, meso-lactide, or racemic lactide, or a mixture thereof. Preferably, the lactide used is L-lactide or meso-lactide or a mixture thereof. Preferably, the lactide is produced from a fermentation process. For at least some applications, L-lactide is most preferred. The hydroxyl containing compound can be a fatty alcohol, such as those containing from about 6 to about 18 carbon atoms. Preferably, the hydroxyl containing compound is a primary alcohol. One example of a preferred fatty alcohol is lauryl alcohol. Also preferably, no solvent is used in the process, and the alkyl lactyllactate produced is a clear, homogeneous liquid.

Another embodiment of a method to make the alkyl lactyllactate of the present technology is the condensation of at least about 4 equivalents of at least one lactic acid component per 1 equivalent of at least one hydroxyl containing compound (e.g., a fatty alcohol or alkoxylated alcohol) component, and relative amounts thereto. Preferably, a catalyst is used. An example of a preferred catalysts is para-toluensulfonic acid. The reaction temperature can be in the range of from about 120° C. to about 200° C. Preferably, no solvent is used in the reaction.

In yet another aspect, the presently describe technology provides a composition comprising at least one alkyl lactyllactate. The composition can be in an aqueous system or in other forms. The composition can further comprise one or more surfactants. The composition can further comprise a buffer. Such a buffer, for example, may comprise a sufficient amount (e.g., about 0.1% to about 0.75% by weight) of citric acid/sodium citrate, lactic acid/ammonium lactate, or a mixture thereof. Preferably, the buffer system should be provided in a sufficient amount to stabilize the pH of the resultant formulation for at least four weeks in a stability test at 50° C. The proper amount of the buffer needed can be determined by routine steps/tests known and appreciated by those skilled in the art, and is dependent on the level of alkyl lactyllactate(s) and/or other actives used in the end-use formulation. Preferably, the alkyl group in the alkyl lactyllactate comprises from about 6 to about 18 carbon atoms, more preferably from about 12 to about 14 carbon atoms, such as a lauryl group. More preferably, the alkyl lactyllactate is an L-alkyl lactyllactate. Most preferably, the composition is substantially free of alkyl lactyllactates of other stereoisomers.

BRIEF DESCRIPTION OF SEVERAL VIEWS OF THE DRAWINGS

FIG. 7 shows comparative study results of the stability of a composition with a buffer and a composition without a buffer.

DETAILED DESCRIPTION OF THE INVENTION

Figure 1:
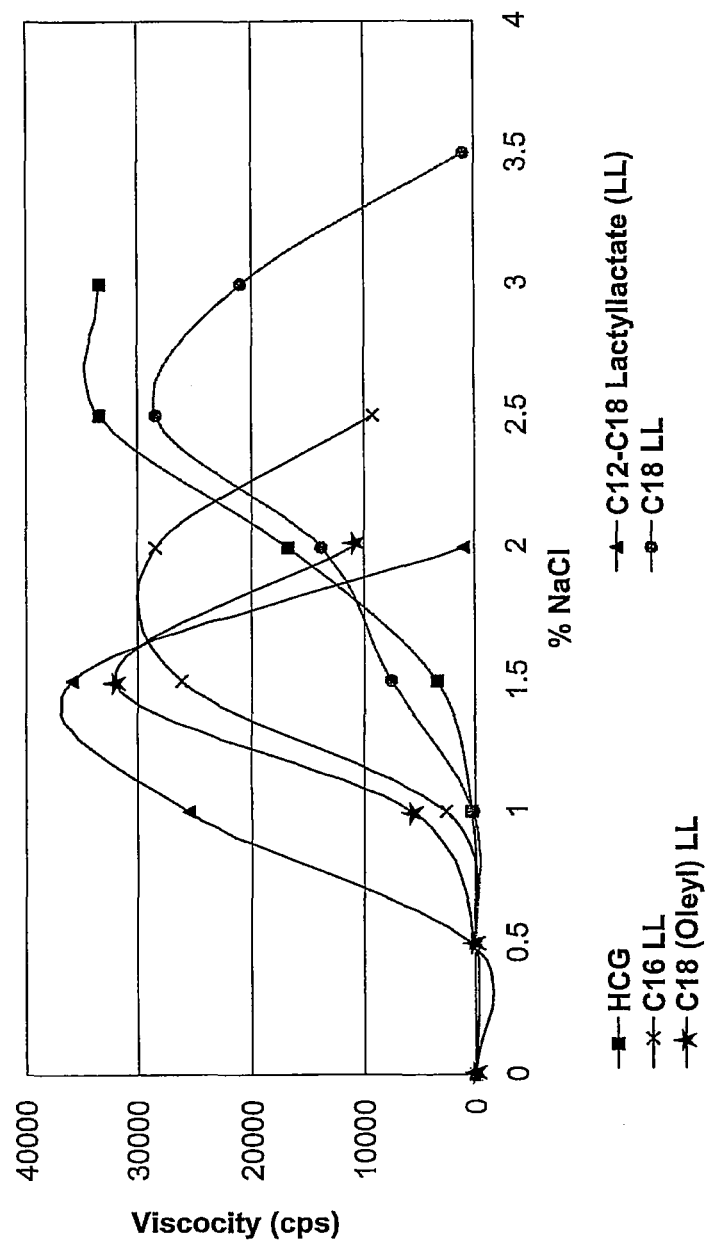
FIGS. 1 and 2 show viscosity salt response curves of exemplary compositions with or without alkyl lactyllactates of the present technology.

In accordance with some embodiments, the alkyl lactyllactates of the present technology can be of the following general structure (I):

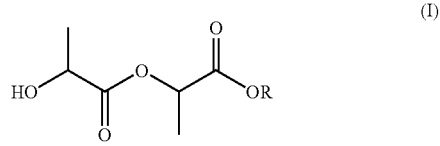

In general structure (I), R comprises an alkyl group or alkoxylated alkyl group. R can be derived from at least one hydroxyl containing compound, such as an alcohol. As used herein, the term "hydroxyl containing compound" refers generally to a compound that contains at least one hydroxyl ("OH") group.

Preferably, the alkyl lactyllactate of the present technology exhibits a specific chirality, which can be, for example, an L-lactyllactate, a D-lactyllactate, an L,D/D,L racemic lactyllactate made from, for example, meso-lactide, or an L,L/D,D racemic lactyllactate made from, for example, racemic lactide, or a mixture thereof. In accordance with at least some applications, L-lactyllactate is most preferred. The alkyl lactyllactates can be prepared from lactide and a hydroxyl containing compound, such as a fatty alcohol, or an alkoxylated alcohol (a "lactide process"). The alkyl lactyllactates can also be prepared directly from lactic acid (a "lactic acid process"). Preferably, the lactic acid used to prepare the lactide or alkyl lactyllactates of the present technology is produced via a fermentation process as known in the art.

The hydroxyl containing compound used to make the alkyl lactyllactates of the present technology can be straight, branched, saturated, or unsaturated, and can be derived from natural or synthetic feed stocks. The alkyl group in the hydroxyl containing compound can preferably include from about 1 to about 22, alternatively from about 6 to about 18, alternatively from about 12 to about 18, alternatively from about 12 to about 14 carbon atoms. The hydroxyl containing compound preferably contains at least one primary hydroxyl group. Preferably, in accordance with at least one embodiment of the present technology, lactide can selectively react with the primary hydroxyl groups in the hydroxyl containing compounds. The hydroxyl containing compounds are preferably substantially free of secondary or tertiary hydroxyl groups. Without intending to be bound by any particular theory, it has been surprisingly found that a secondary or tertiary hydroxyl alcohol can cause a polymerization problem when the lactide reacts with the hydroxyl containing compound, for example, at an equal molar ratio. More preferably, in accordance with some embodiments, the hydroxyl containing compounds are primary fatty alcohols, and most preferably, C12-C14 fatty alcohols to avoid the polymerization problem in making one or more of the alkyl lactyllactates of the present technology.

It has also been found that fatty alcohols, in particular C12 or C14 or C12/C14 alcohols, can provide alkyl lactyllactates exhibiting improved and desired foaming, detergency, skin feel, and/or physical properties (e.g., viscosity building, solubility, and formulatability) for use in, for example, personal care, home care, and other cleansing applications. Although not intending to be bound by any particular theory, it is believed that C12/C14 lactyllactates of the present technology can provide the best overall performance for at least some end-use applications (e.g., body washes, shampoos, etc.). It is also believed that an alkyl lactyllactate made from C16 or C16/C18 can produce a better feel, but less foam, for example. In addition, C12/C14 lactyllactates are liquid at room temperature, while C16/C18 lactyllactates are solids at room temperature. When lower alcohols are used, the resulting alkyl lactyllactates can still provide good foaming performance, but their viscosity building properties may be worse than C12/C14 lactyllactates. Examples of suitable fatty alcohols include lauryl alcohol and stearyl alcohol.

In addition, it is preferable that no solvent is used in the lactide processes of the present technology to make the desired alkyl lactyllactates. It is an object of the present technology to eliminate the use of a solvent in the reaction process for producing alkyl lactyllactates for at least some applications, such as personal care applications. However, typically, a solvent free process can be difficult to operate because of viscosity or product distribution concerns. In the presently described technology, it has been surprisingly found that a reaction product with the desired lactyllactate to lactate or higher polymer distribution can be obtained by using a solvent-free reaction system. The alkyl lactyllactate product produced by the lactide processes of the present technology preferably contains more than about 90% of at least one alkyl lactyllactate and less than about 10% of alkyl lactate(s), higher polymer(s) and other impurity components, based on the total weight of the reaction product.

By way of further example, the hydroxyl containing compounds of the present technology may be alkoxylated alcohols, for example, alcohols that are ethoxylated, propoxylated or both. The hydroxyl containing compounds can be alkoxylated in situ when reacting with lactide. Alternatively, preformed alkoxylated hydroxyl containing compounds can be used. For example, ethoxylated lauryl alcohols can be used to produce ethoxylated lauryl lactyllactates (LLL(EO)) containing a specific amount, which preferably is from about 1 to about 12 (e.g., 1 mole, 2 moles, or 3 moles), of ethoxylate (EO) per mole of the lactyllactate (e.g., LLL (1EO), LLL (2EO), or LLL (3EO)).

Alkoxylation can change, among other things, the polarity of an alkyl lactyllactate molecule, which can make the resulting lactyllactate molecule more water soluble and affect its hydrophilic/lipophilic balance (HLB). It can also affect the packing of a surfactant in a micelle. Alkoxylation can further affect the wetting ability, cloud point, and other surfactant properties of the alkyl lactyllactate. Without intending to be bound by any particular theory, it is believed that alkoxylation can allow for emulsion with lower surfactant actives or microemulsion, improved clarity, and better stability. The cleaning performance of a lactyllactate surfactant may also be affected, and the ability to tailor properties of the surfactant is increased.

In accordance with some embodiments, the alkyl lactyllactate of the present technology can be represented by the following general structure (II):

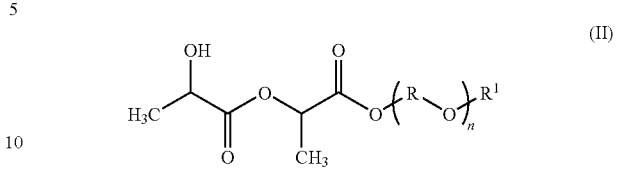

In the general structure (II), R preferably contains about two to about six, more preferably about two to about four, most preferably about two to about three carbon atoms, $R^1$ preferably contains about one to about twenty two, alternatively about one to about eighteen, alternatively about six to about eighteen, alternatively about twelve to about fourteen, alternatively about one to about six carbon atoms (e.g., four carbon atoms), and the number of repeat units (n) preferably can vary from about 0 to about 100. When n is 0, $R^1$ preferably contains about 12 to about 18, alternatively about 12 to about 14 carbon atoms. When n is not 0, the alkyl lactyllactates contains at least one alkoxylate group, and preferably, n is from about one to about twelve, alternatively from about one to about six, alternatively from about two to about 4; $R^1$ preferably contains about one to about six carbon atoms (e.g., butanol+1 EO, butanol+2EO, ethanol+2EO, hexanol+2EO), alternatively, $R^1$ contains about 6 to about 18 carbon atoms.

In some embodiments, the R group in the general structure (I) or the $R^1$ group in the general structure (II) above can be derived from a diol with two primary hydroxyl groups (OH's) or a polyol containing two or more primary OH's. In some other embodiments, the R group can be derived from diols or polyols containing at least one primary OH. For example, when a compound containing two primary hydroxyl groups (e.g., glycerin or ethoxylated glycerin) is used as the bridging molecule, the alkyl lactyllactate in accordance with some embodiments of the present technology can be represented by the following general structure (III):

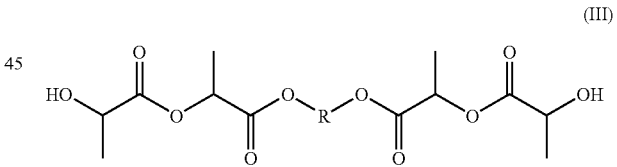

In accordance with some embodiments, the R group in the above formula (III) can preferably contain from about two to about twenty-four, preferably from about two to about eight carbon atoms, and R can be an alkyl group or an alkoxylated alkyl group. For example, the R group can be derived from glycerin or ethoxylated glycerin.

Different forms of lactide, such as L-lactide, D-lactide, meso-lactide, racemic lactide, or a mixture thereof can be used to produce the alkyl lactyllactates of the present technology. L-lactide, meso-lactide, or a mixture thereof is preferred. More preferably, the lactide used in the presently described technology is made from lactic acid or a derivative thereof produced from a fermentation process such as a carbohydrate fermentation or biofermentation process known in the art. Derivatives of lactic acid that may be used to produce lactides include, for example, lactate esters and ammonium lactate obtained by lactic fermentation.

In at least one embodiment of the present technology, L-lactide or a mixture of L-lactide and meso-lactide is most preferred to produce alkyl lactyllactates with, for example, better foaming and/or better viscosity building properties. Thus, for some personal care applications, lactyllactates made from L-lactide or a mixture of L-lactide and meso-lactide are most preferred. In some other embodiments, alkyl lactyllactates made from meso-lactide can be preferred. For example, for light duty laundry (LDL) detergent, high duty laundry (HDL) detergent, some soap bar applications, or some solvent applications, alkyl lactyllactates produced from meso-lactide can be preferably used. Meso-lactide and mixtures of L-lactide and meso-lactide are normally in liquid form at room temperature, while L-lactide, racemic lactide, and D-lactide are solids at room temperature. Without intending to be bound by any particular theory, it has been observed that a mixture of meso-lactide and L-lactide reacts faster than a pure L-lactide under identical reaction conditions.

The reaction temperatures for producing alkyl lactyllactates of the present technology can be in the range of from about 15° C. to about 150° C., alternatively from about 20° C. to about 100° C., alternatively from about 25° C. to about 75° C., alternatively from about 30° C. to about 70° C. In accordance with at least some embodiments (e.g., to make alkyl lactyllactates for personal care applications), the reaction temperature preferably is in the range of from about 40° C. to about 60° C., alternatively from about 50° C. to about 60° C., alternatively from about 40° C. to about 50° C.

An acid catalyst is preferably used in the reaction of lactide and hydroxyl containing compounds. Examples of acid catalysts include, but are not limited to, $H_2SO_4$, HCl, p-toluenesulfonic acid (pTSA), and NAFION® ionomers (available from E.I. du Pont de Nemours and Company). In accordance with at least some embodiments, the amount of catalyst needed for one or more processes of the present technology is about 1.0 wt % or less, alternatively from about 0.01 wt % to about 0.4 wt %, based on the weight of lactide in the reaction mixture.

Alkyl lactyllactates made from L-lactide are most preferred for at least some embodiments of the present technology, especially for personal care applications. For some personal care applications, alkyl lactyllactates made from a mixture of L-lactide and meso-lactide can also be preferably used. It has been unexpectedly discovered that alkyl lactyllactates made from L-lactide or a mixture of L-lactide and meso-lactide have better foaming and/or better viscosity building properties than the racemic alkyl lactyllactates made from meso-lactide or racemic lactide. When a mixture of L-lactide and meso-lactide is used, the amount of L-lactide in the mixture can be from about 50% to about 100%, alternatively from about 0% to about 70%, alternatively from about 15% to about 70%, based on the total weight of the L-lactide and meso-lactide. The scheme below illustrates a process of the present technology for producing L-alkyl lactyllactates. In this exemplary scheme, L-lactide reacts with a $C_{6-18}$ fatty alcohol (ROH) at 50° C. in the presence of $H_2SO_4$, as the catalyst, for approximately 12 to 24 hours to produce an L-alkyl lactyllactate.

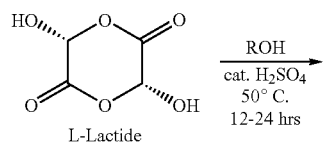

L-Lactide

-continued

L-alkyl Lactyllactate

Other lactides such as D-lactide, meso-lactide and racemic lactide can produce alkyl lactyllactates with different stereochemistry (stereoisomers). In at least one embodiment of the present technology, alkyl lactyllactates made from meso-lactide are preferred. In the following exemplary scheme, meso-lactide reacts with a $C_{12-18}$ fatty alcohol (ROH) at 50° C. in the presence of $H_2SO_4$, as the catalyst, for approximately 12 to 24 hours to produce an L,D/D,L rac-alkyl lactyllactate. Another form of rac-alkyl lactyllactate (L,L/D,D) can be produced by reacting racemic lactide with the fatty alcohol.

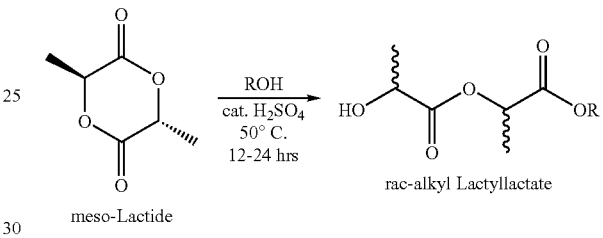

meso-Lactide       rac-alkyl Lactyllactate

It has been discovered that the processes of the presently described technology can substantially reduce or avoid the production of by-products and unexpectedly increase the production yield and product purity of the targeted alkyl lactyllactate. For example, it has been discovered that the reaction of lactide with a hydroxyl containing compound (e.g., L-lactide with lauryl alcohol) in accordance with the present technology can preferably achieve a yield of about 95% or more, and the purity of alkyl lactyllactate(s) in the product mixture without further purification can preferably reach about 90% or more, alternatively about 95% or more, based on the total weight of the product mixture. The amount of either the alkyl lactate by-product or the remaining alcohol is preferably less than about 5% (e.g., in the range of from about 1% to about 5%) based on the total weight of the product mixture.

In accordance with at least one embodiment of the present technology, equivalent moles of lactide, e.g., solid L-lactide, and at least one fatty alcohol are combined at an elevated temperature (e.g., 50° C.) with a catalytic amount (approximately about 0.01% to about 1% by weight based on the weight of the lactide) of sulfuric acid. Different molar ratios of the lactide and the alcohol(s), for example, an excess amount of the lactide or the alcohol(s), can be used. However, equivalent amounts of lactide and alcohol(s) are preferred for at least some embodiments of the present technology. The reaction stops after, for example, approximately 12 to 24 hours (e.g., approximately 16 hours), when the mixture becomes a hazy to clear, homogeneous liquid, preferably a clear homogeneous liquid. If the mixture is hazy, then the mixture can be heated at an elevated temperature (e.g., 50-60° C.) for an extended period of time to generate the preferred clear, homogenous liquid. Generally, the lower the reaction temperature, the longer the reaction time is needed. The mixture can be used in personal care and other applications. The residual sulfuric acid can be left in, or removed by, for example, water washing, adsorption onto basic alumina or silica media, or via neutralization with a base.

In accordance with at least one other embodiment of the present technology, lactide and a hydroxyl containing compound with two or more hydroxyl groups can be condensed in a 1:1 or higher molar ratio to make the alkyl lactyllactate of the present technology. The hydroxyl containing compound can be a fatty alcohol or alkoxylated alcohol, and can be a polyol or alkoxylated polyol containing two or more hydroxyl groups, preferably two or more primary hydroxyl groups. Preferably, equivalent molar amounts of the lactide and the hydroxyl containing compound are used. Alternatively, an excess amount of the hydroxyl containing compound or lactide can be used, but doing so is less preferred for at least some applications.

Alternatively, alkyl lactyllactates of the present technology can be made from lactic acid (e.g., L-lactic acid, D-lactic acid, or racemic lactic acid) and a hydroxyl containing compound such as an alcohol. The reaction product normally comprises a mixture of alkyl lactyllactate(s) and alkyl lactate(s). The presently described technology provides improved processes for making alkyl lactyllactates via a lactic acid route. In the presently described technology, a process for making alkyl lactyllactates via a lactic acid route can be referred to as the lactic acid process, while a process via a lactide route can be referred to as the lactide process. It has been found that a reaction product produced by one or more of the lactic acid processes of the present technology has an unexpectedly increased ratio of alkyl lactyllactate(s) over alkyl lactate(s) than that can be achieved by processes of the prior art.

Hydroxyl containing compounds as introduced above, including primary, secondary, or tertiary alcohols, can be utilized to react with the lactic acid. It has been discovered that at least in some embodiments, the ratio of alkyl lactyllactate(s) vs. alkyl lactate(s) in the reaction product can be improved by utilizing a primary alcohol. Similar to the lactide processes described above, preferably, no solvent is employed in a process using the lactic acid to produce the alkyl lactyllactate of the present technology. It has been surprisingly found that a reaction product with the desired lactyllactate to lactate and/or higher polymer distribution can be obtained by the lactic acid process of the present technology using a solvent-free reaction system. The alkyl lactyllactate product produced by the lactic acid processes of the present technology preferably contains at least about 40%, alternatively at least about 50% alkyl lactyllactate(s), based on the total weight of the alkyl lactyllactate(s) and alkyl lactates in the product, and has an alkyl lactyllactate to alkyl lactate ratio of greater than about 0.5:1, more preferably greater than about 0.8:1, most preferably greater than about 1:1, as determined by GC analysis.

The lactic acid process of the present technology differs from the prior art in, for example, that a catalyst (e.g., para-toluenesulfonic acid) is used and/or a higher ratio of lactic acid to the hydroxyl containing compound(s) is used. These two reaction variables can increase the amount of alkyl lactyllactate(s) (e.g., lauryl lactyllactate (L3)) produced in the reaction, and decrease the amount of alkyl lactate(s) (e.g., lauryl lactate (L2)) produced. Examples of catalysts that can be used include, but are not limited to, sulfuric acid ($H_2SO_4$), HCl, methanesulfonic acid, $BF_3$ etherate, para-toluenesulfonic (pTSA), phosphoric acid, and NAFION® ionomers. Methanesulfonic acid, $BF_3$ etherate, and pTSA are preferred. In at least one embodiment, pTSA is most preferred. Preferably, at least about four equivalents, alternatively at least about six equivalents, alternatively at least about eight equivalents, of lactic acid per one equivalent of the hydroxyl containing compound(s) (e.g., a fatty alcohol or a mixture of fatty alcohols) are used.

L-lactic acid is preferred at least for some applications (such as personal care applications) of the present technology, but D-lactic acid or racemic lactic acid can also be used. Preferably, the lactic acid is made by a fermentation process. The reaction temperature of the lactic acid process is preferably in the range of from about 120° C. to about 200° C., alternatively from about 180° C. to about 185° C.

The alkyl lactyllactate composition obtained using the lactic acid process of the present technology is different from alkyl lactyllactate compositions obtained in the lactic acid processes of the prior art (e.g., U.S. Pat. No. 3,144,341), and contain substantially more lactyllactate content. For example, reaction products of the lactic acid processes of the present technology can preferably contain at least about 40%, alternatively at least about 50% alkyl lactyllactates, based on the total weights of the alkyl lactyllactates and alkyl lactates in the desired reaction products. In a comparative study, it was found that reaction products produced from the lactic acid process described in U.S. Pat. No. 3,144,341 only contained about 20% or less alkyl lactyllactates, based on the total weights of the alkyl lactyllactates and alkyl lactates in the reaction products. Because of the higher amounts of the alkyl lactyllactate component, the alkyl lactyllactate compositions produced by the lactic acid processes of the present technology can exhibit different and/or superior properties than the alkyl lactyllactate compositions produced by the lactic acid processes of the prior art. For example, when the reaction products of the lactic acid processes of the present technology are used in personal or home care applications, they can lead to improved viscosity building as compared to the reaction products of the lactic acid processes of the prior art.

The alkyl lactyllactate of the present technology can be in different forms depending upon the starting materials. For example, it can be a chiral lactyllactate made by reacting a chiral lactide (L- or D-lactide) with an alcohol, a racemic lactyllactate made by reacting meso-lactide or racemic lactide with an alcohol, a mixture of alkyl lactyllactates made by reacting a mixture of L-lactide and meso-lactide with an alcohol, and a mixture of alkyl lactate and alkyl lactyllactate by reacting a lactic acid with an alcohol using the processes of the present technology. The alcohol preferably contains at least one primary hydroxyl group. More preferably, the alcohol is a fatty alcohol.

It has been surprisingly found that the alkyl lactyllactates of the present technology, such as the lauryl lactyllactate, are ideal for use as surfactants. The preferred alkyl lactyllactates of the present technology are naturally derived, and substantially salt free. An alkyl lactyllactate of the present technology preferably has a specific chirality, and can be an L-lactyllactate, a D-lactyllactate, an L,D/D,L racemic lactyllactate, an L,L/D,D racemic lactyllactate, or a mixture thereof. In accordance with at least some embodiments, an alkyl lactyllactate product produced by the lactide processes of the present technology preferably contains more than about 90% alkyl lactyllactate(s) and less than about 10% alkyl lactate(s), based on the total weight of the product. Alternatively, an alkyl lactyllactate of the present technology can be a mixture of alkyl lactyllactate(s) and alkyl lactate(s) produced by the lactic acid processes of the present technology. Preferably, a reaction product mixture produced by the lactic acid processes has a lactyllactate to lactate ratio of greater than about 0.5:1, more preferably greater than about 0.8:1, most preferably greater than about 1:1 (e.g., about 1.4:1), as determined by GC analysis. Without intending to be bound by any particular theory, it is believed that in some applications, such as in hard surface cleaners, the inclusion of some alkyl lactate in a surfactant composition can increase the composition's performance by improving the ability of surfactants to pack in micelles.

At least some preferred alkyl lactyllactate compounds of the present technology are a clear, colorless liquid at room temperature, and are nitrogen free, salt free and 100% active. Preferably, the alkyl lactyllactates can be formulated in cold-mix applications. At least some alkyl lactyllactates of the present technology can provide improved performance (e.g., better skin feel, improved skin sloughing, enhanced foaming, improved viscosity building properties, etc.), improved cost structure (e.g., by reducing the amount of actives), and/or improved stability. Further, at least some of the alkyl lactyllactates are as mild or milder than conventional secondary surfactants such as alkyl ethersulfate, betaines, amphoacetates, amides, or sulfosuccinates. The alkyl lactyllactates of the present technology may also be used as emulsifiers or skin feel agents. For household, industrial and institutional cleaning products, at least some of the alkyl lactyllactates of the present technology can provide improved properties because of their surfactant properties as described above. In addition, they also can improve, for example, wetting or other surface modification, and aid in emulsification or dispersion of soils/particulates or other formulation ingredients.

At least some alkyl lactyllactates of the present technology can be used as a rheological modifier to increase or reduce the viscosity of a composition as desired. It has been found that comparable viscosity values of a surfactant system can be achieved with significantly lower levels of electrolytes (e.g., NaCl) by incorporating at least one alkyl lactyllactate of the present technology into the surfactant system. On the other hand, it has also been found that by incorporating at least one alkyl lactyllactate of the present technology in a fabric softener, the viscosity of the fabric softener composition can be significantly reduced.

Examples of personal care products and other applications that can contain the alkyl lactyllactates of the present technology include, but are not limited to:

Personal cleansing products (such as bar soap, bubble bath, shampoo, body wash, facial cleanser, hand soap, shower gel, wipes, baby cleansing products, etc.);

Creams/lotions (such as lotion with sun-screen protection, anti-aging creams (AHA, BHA), lightening lotion, brightening lotion, lotion with anti-oxidants, tanning lotion, etc.);

Cosmetic products (such as make-up, mascara, lipstick, etc.);

Hair treatment products (such as hair conditioners, hair spray, hair gel, etc.);

Home care or industrial or institutional products (dishwashing detergents, laundry detergents, heavy duty detergents, light duty detergents, fabric softeners, spot treatments, hard surface cleaners, degreasers and/or disinfectants such as those used in the kitchen for countertops, appliances, floors and walls, and bathroom cleaners and disinfectants such as those used for toilets, tubs, showers, floors and walls, polishes, etc.);

Anti-perspirant/deodorants (solid, roll-on, etc.); and

Bath oils and hair shine.

A personal cleansing or home care product such as a shampoo, soap bar, or hard surface cleaner, preferably contains about 0.01% to about 30%, alternatively about 0.01% to about 20%, alternatively about 0.01% to about 10%, alternatively about 0.1% to about 2%, alternatively about 0.01% to about 0.5%, of the alkyl lactyllactate of the present technology, based on the total weight of the product. A liquid dish detergent or laundry detergent, preferably contains about 0.1% to about 40%, alternately about 0.1% to about 30%, alternately about 0.1% to about 25%, alternatively about 0.1% to about 20%, alternately about 1% to about 25%, alternately about 3% to about 20%, of the alkyl lactyllactate of the present technology, based on the total weight of the product.

A cream/lotion product preferably contains about 0.01% to about 75%, alternatively about 0.01% to about 60%, alternatively about 0.01% to about 50%, alternatively about 0.01% to about 40%, alternatively about 0.01% to about 30%, of the alkyl lactyllactate of the present technology, based on the total weight of the product.

A bath oil or hair shine product preferably contains from about 0.01% to about 100%, alternatively from about 1% to about 80% by weight of at least one alkyl lactyllactate of the present technology.

A hair treatment product such as a hair conditioner, a hair gel, or a hair spray, preferably contains about 0.01% to about 35%, alternatively about 0.01% to about 25%, alternatively about 0.01% to about 15%, of at least one alkyl lactyllactate of the present technology, based on the total weight of the product.

A solid anti-perspirant preferably contains about 0.01% to about 80%, alternatively about 0.01% to about 50%, alternatively about 0.01% to about 35%, of at least one alkyl lactyllactate of the present technology, based on the total weight of the product.

A roll-on anti-perspirant, on the other hand, preferably contains about 0.01% to about 20%, alternatively about 0.01% to about 10%, alternatively about 0.01% to about 5%, of at least one alkyl lactyllactate of the present technology, based on the total weight of the product.

A cleansing composition comprising the alkyl lactyllactate of the present technology preferably further contains at least one or more other organic or inorganic surfactants such as anionic, cationic, nonionic, amphoteric or zwitterionic surfactants, derivatives thereof, or mixtures thereof. These surfactants are known in the art, and are described in, for example, U.S. Pat. No. 3,929,678 (Laughlin et al.), which is incorporated herein by reference. Examples of useful cationic surfactants also include those described in U.S. Pat. Nos. 4,295,217 (Murphy) and 4,222,905 (Cockrell), both of which are incorporated herein by reference. In accordance with some embodiments, the one or more other surfactants in a cleansing composition can represent from about 1% to about 95%, alternatively from about 2% to about 70%, alternatively from about 2% to about 30%, alternatively from about 3% to about 10%, by weight of the cleansing composition.

Examples of popular nonionic surfactants for use with the present technology include, but are not limited to, alkyl phenol ethoxylates, alcohol alkoxylates $C_{8-18}$ EO 2-12, alkyl dimethyl or alkyl amidopropyl dimethyl amine oxides, MEA or DEA type alkanolamide, alkyl polyglycoside, ethoxylated alkanolamides, and mixtures thereof. For laundry and hard surface cleansing compositions, alcohol alkoxylates and amine oxides, for example, are preferred.

Examples of anionic surfactants include, but are not limited to, alcohol sulfates, alcohol alkoxy sulfates, alkylbenzene sulfonates, alpha olefin sulfonates, alpha sulfo methyl or ethyl esters of C8 through C8 fatty acids (mono and/or disalts), sulfosuccinates, and mixtures thereof. Preferably, the alkyl groups in the anionic surfactants have from about 8 to about 18 carbon atoms. The counter ions for the anionic surfactants can be, for example, sodium, potassium, triethanol amine, monoethanol amine, ammonia, magnesium, etc. For laundry and liquid dishwashing detergents, preferred anionic surfactants include, but are not limited to, alkylbenzene sulfonates, alkyl ethoxy sulfates, and alpha sulfo methyl ester C12-18. For hard surface cleansing compositions, preferred anionic surfactants include, for example, alkylbenzene sulfonates, alcohol sulfates, and alkyl ethoxy sulfates.

Examples of amphoteric surfactants include, but are not limited to, sultaines, betaines, alkyl dimethyl or alkyl amidopropyl dimethyl betaines, alkyl dimethyl or alkyl amidopropyl dimethyl amine oxides, mono- or di-sodium alkyl ampho (mono- or di)acetates; proprionates, sarcosinates, and mixtures thereof. For liquid dishwashing detergents, preferred amphoteric surfactants include, for example, betaines and amine oxides. For laundry detergents and hard surface cleansing compositions, preferred amphoteric surfactants include, for example, amine oxides.

Examples of quaternary ammonium compounds (quats) that can be used in combination with the alkyl lactyllactates of the present technology include, but are not limited to, dialkyl dimethyl ammonium chlorides, alkyl dimethyl benzyl/ethyl benzyl ammonium chlorides, alkyl dimethyl benzyl ammonium chlorides, and mixtures thereof. When the products containing the alkyl lactyllactates of the present technology are hard surface disinfectants or sanitizers, the quaternary ammonium compounds are preferably registered antimicrobial products, and should be used at an effective amount to kill the targeted organisms.

Anionic and zwitterionic surfactants are preferred surfactants to be used in combination with the alkyl lactyllactates of the present technology for cleansing compositions because of their ability to provide foam and remove the particulate soil from skin and hair without inducing dryness or irritation. Useful anionic surfactants specifically include those described in U.S. Pat. No. 3,929,678 (Laughllin et al.) and those described in U.S. Pat. No. 4,199,483 (Jones), which are incorporated herein by reference.

When an alkyl lactyllactate of the present technology is used as a co-surfactant in a personal care liquid cleansing composition in accordance with at least one embodiment of the present technology, the personal care liquid cleansing composition preferably comprises about 0.1% to about 95%, alternatively about 1% to about 70%, alternatively about 1% to about 30%, alternatively about 1% to about 10%, alternatively about 1% to about 5%, of other surfactants; and about 0.1% to about 15%, alternatively about 0.1% to about 5%, alternatively about 0.1% to about 2%, of at least one alkyl lactyllactate of the present technology. The very low concentrations for the bottom ranges can be used, for example, when finger pump foamers are used as the packaging systems. It is known to those skilled in the art that finger pump foamers are very efficient packaging systems that can deliver excellent foam at very low surfactant concentrations. Production costs can be reduced with such delivery systems.

Examples of preferred detergent systems for personal care cleansers are readily known to those skilled in the art and can include combinations of anionic surfactants and zwitterionic co-surfactants. U.S. Pat. No. 5,705,147 (Shapiro, et al.) incorporated herein by reference provides a detailed description of such surfactants used to prepare personal care cleansers. The alkyl lactyllactates of the presently described technology, when incorporated in formulations containing mixtures of the surfactants described in U.S. Pat. No. 5,705,147 (Shapiro, et al.), for example, can provide enhancement in organoleptic characteristics of viscosity, flow-ability and foam stability. A brief list of typical surfactants for personal care detergents would include alkyl and aryl-sulfates and sulfonates, alkyl and aryl ether sulfates, derivatives of aliphatic quaternary ammonium compounds known in the art as betaines.

A detergent composition comprising the alkyl lactyllactate of the present technology preferably contains from about 0.01% to about 10%, alternatively from about 0.1% to about 5% actives of at least one alkyl lactyllactate based upon the total weight formulation.

For example, a heavy duty or light duty liquid detergent formulation of the present technology preferably contains lauryl lactyllactate (L3) available from Stepan Company, Northfield, Ill. under the trade name STEPAN-MILD® L3, as a co-surfactant in conjunction with anionic surfactants. In such applications, lauryl lactyllactate(s) can be present in an amount of, for example, 1.5% actives for a heavy duty laundry formulation without enzyme; and in an amount of, for example, 3% or 1.5% for a light duty laundry or hand dishwashing formulation, based upon the total weight of the formulation. Examples of suitable anionic surfactants for use in such formulations include, but are not limited to, dodecylbenzene sulfonate, sodium laureth sulfate (3 EO), sodium laureth sulfate (2 EO), and sodium methyl-2-sulfopalmitate/disodium 2-sulfopalmitate.

As another example, lauryl lactyllactate can be used as a secondary surfactant in ultra dish wash detergent formulations in amounts less than about 0.5% actives based upon the total formulation, such as, for example, as low as about 0.1% actives based upon the total formulation. These ranges are appropriate when lauryl lactyllactate is the only secondary surfactant in the formulation, as well as in applications where lauryl lactyllactate is incorporated in conjunction with additional secondary surfactants. In contrast, conventional ultra dish wash detergent formulations typically contain secondary surfactant(s) in an amount from about 0.5% actives to about 3.5% actives based upon the total weight of the formulation.

The alkyl lactyllactates of the present technology can be used as co-surfactants in compositions comprising different primary surfactants such as alkyl sulfates, alkyl ether sulfates, olefin sulfonates, alkyl benzene sulfonic acids, alkyl benzene sulfonates, and alkali metal, alkaline earth metal, amine and ammonium salts thereof. Examples of primary surfactants include, but are not limited to, sodium lauryl sulfate (SLS), sodium laureth sulfates (SLES), sodium coco sulfate, sodium lauryl glucose carboxylate, sodium lauryl glucoside, ammonium laureth sulfates, triethanolamine lauryl sulfate, polydecyl glucoside carboxylate, derivatives thereof, and combinations thereof. The alkyl lactyllactates of the present technology can be used to substitute or in combination with conventional or new secondary surfactants such as amides, betaines, sultaines, and alkyl polyglucosides. Examples of secondary surfactants that can be replaced or supplemented by the alkyl lactyllactates of the present technology include, but are not limited to, cocamidopropyl betaine, acyl lactylates such as sodium lauroyl lactylate, amphoacetates such as sodium cocoamphoacetate, sulfosuccinates such as sodium di(2-ethylhexyl) sulfosuccinate, lauryl glucoside, sodium cocoyl glutamate, monoethanol and diethanol based amides such as cocamide monoethanolamide, derivatives thereof, and combinations thereof.

It has been surprisingly found that a surfactant blend comprising an alkyl lactyllactate or a mixture of alkyl lactyllactates of the present technology (e.g., lauryl lactyllactate) has a significantly lower critical micelle concentration (CMC) than those that do not contain alkyl lactyllactate. For example, compositions comprising the alkyl lactyllactates of the present technology have exhibited a reduction in critical micelle concentration of from about 5% to about 99%, alternatively from about 30% to about 99%, alternatively from about 85% to about 99%, as compared to a comparative surfactant solution without the alkyl lactyllactate. A comparative surfactant solution can be a composition that contains substantially the same concentration of the same surfactant actives as the composition of the present technology under study, but does not contain the alkyl lactyllactates of the present technology. Thus, without intending to be bound by any particular theory, it is believed that at least some of the alkyl lactyllactates of the present technology can improve detergency, and potentially improve mildness of the primary surfactants.

Typically, surfactants have the tendency to occupy space at the air/water or liquid/liquid interface. Each surfactant molecule occupies a certain surface area, which is dominated by the molecular structure of a surfactant. In the case of a surfactant mixture, the area per molecule (area/molecule) depends not only on the molecular structure of each individual surfactant molecule, but also on how different molecules are arranged and interact with each other. When the interactions between molecules reduce the total repulsion forces, then each surfactant molecule can occupy smaller area at the interface. This phenomena is called "reduce area/molecule".

It has been surprisingly found that at least some alkyl lactyllactates of the present technology (e.g., lauryl lactyllactate) can improve the molecular packing of primary surfactant at the air/water interface and reduce the area/molecule in a surfactant blend. For example, some compositions comprising the alkyl lactyllactates of the present technology have exhibited a reduction in the area per molecule of from about 2% to about 80%, alternatively from about 10% to about 60% (e.g., 35% or 45%), as compared to a comparative surfactant solution without the alkyl lactyllactate.

Further, it has been unexpectedly discovered that a surfactant system containing an alkyl lactyllactate of the present technology and a primary surfactant (e.g., SLES-2) can saturate the air/water interface faster and have a lower dynamic surface tension (at the same use level) than a conventional surfactant system containing, for example, a betaine or amide and SLES-2. Thus, without intending to be bound by any particular theory, it is believed that at least some of the alkyl lactyllactates of the present technology can potentially improve flash foam, and foam volume, of a surfactant system. It has also been unexpectedly discovered that lactyllactates made from L-lactide or mixtures of L-lactide and meso-lactide can produce foam better than rac-lactyllactates.

In accordance with at least one embodiment of the present technology, a composition comprising an alkyl lactyllactate of the present technology and a primary surfactant in an aqueous system can further comprise a buffer to improve the high temperature stability of the composition. Any primary surfactants and buffering agents suitable for personal care, home care, or industrial and institutional products can be used. Examples of buffering systems include, but are not limited to, a citric acid/sodium citrate buffer, a lactic acid/ammonium lactate buffer, or a combination thereof. Without intending to be bound by any particular theory, it has been observed in the present technology that the high temperature stability of the composition can be greatly extended by using a buffer. For cleansing applications, each surfactant system can have a different buffer system with a different concentration. The proper amount of the buffer needed can be determined by known testing appreciated by those skilled in the art, and is dependent on the level of lactyllactate and other actives used in a formulation. In general, the level of the buffer can be in the range of from about 0% to about 1%, alternatively from about 0.1% to about 0.75%, alternatively from about 0.1% to about 0.5%, based on the weight of the formulation.

In addition to aqueous systems, the alkyl lactyllactates of the present technology can also be formulated into a solid, a gel, or other forms of personal care products or other applications. For example, the alkyl lactyllactates of the present technology can be added into soap bars as a co-surfactant. Compared to conventional secondary surfactants for soap bars such as cocamidopropyl betaine and cocamide monoethanolamide, at least some alkyl lactyllactates of the present technology (e.g., lauryl lactyllactate (L3) available from Stepan Company under the trade name STEPAN-MILD® L3) can exhibit improved foaming performance, and directional improvement in most skin feel attributes. It has been found that at least some alkyl lactyllactates of the present technology (e.g., alkyl lactyllactates made from L-lactide or a mixture of L-lactide and meso-lactide) can improve the plasticity of soap bars during processing, which suggests a positive impact on bar cracking, clipping, and peeling without affecting rinsability and wet feel properties.

In accordance with some embodiments of the present technology, a soap bar preferably comprises (1) about 0.01 to about 30% of the alkyl lactyllactate of the present technology, (2) about 0 to about 50% of a synthetic surfactant, (3) about 0 to about 30% of at least one alpha sulfonated alkyl ester, at least one sulfonated fatty acid, or a mixture thereof, (4) about 30% to about 95% of a C6-C22 soap, (5) about 0.5% to about 30% of a C6-C22 fatty acid, (6) about 0.1% to about 5% of an electrolyte, (7) about 0.5% to about 15% of a polyhydric alcohol, and (8) about 3% to about 22% of water, all based on the total weight of the soap bar.

Alternatively, the soap bar can comprise: (1) about 0.01 to about 10% of the alkyl lactyllactate of the present technology, (2) about 0 to about 20% of a synthetic surfactant, (3) about 0 to about 15% of at least one alpha sulfonated alkyl ester, at least one sulfonated fatty acid, or a mixture thereof, (4) about 30% to about 95% of a C6-C22 soap, (5) about 0.5% to about 10% of a C6-C22 fatty acid, (6) about 0.1% to about 3% of an electrolyte, (7) about 0.5% to about 10% of a polyhydric alcohol, and (8) about 3% to about 22% of water, all based on the total weight of the soap bar.

Alternatively, the soap bar can comprise: (1) about 0.01 to about 5% of the alkyl lactyllactate of the present technology, (2) about 0 to about 10% of a synthetic surfactant, (3) about 0 to about 10% of at least one alpha sulfonated alkyl ester, at least one sulfonated fatty acid, or a mixture thereof, (4) about 30% to about 95% of a C6-C22 soap, (5) about 0.5% to about 5% of a C6-C22 fatty acid, (6) about 0.1% to about 2% of an electrolyte, (7) about 0.5% to about 6% of a polyhydric alcohol, and (8) about 3% to about 22% of water, all based on the total weight of the soap bar.

In accordance with at least one other embodiment, the one or more alkyl lactyllactates of the present technology can be included in an all-purpose cleaner concentrate in an amount of, for example, from about 0.01% to about 10%, alternatively from about 0.1% to about 5% actives based on the total weight of the concentrate.

In accordance with at least one other embodiment, the one or more alkyl lactyllactates of the present technology can be included in a ready-to-use cleaner in an amount of, for example, from about 0.01% to about 10%, alternatively about 0.1% to about 5% actives based on the total weight of the cleaner.

One or more alkyl lactyllactates of the present technology can also be included in a glass cleaner in an amount of, for example, from about 0.01 to about 2% actives based on the total weight of the cleaner.

Further, one or more alkyl lactyllactates of the present technology can be included in a bathroom cleaner in an amount of, for example, from about 0.01 to about 10% actives based on the total weight of the cleaner.

Moreover, one or more alkyl lactyllactates of the present technology can also be included in a liquid scouring cleaner in an amount of, for example, from about 0.01 to about 10% actives based on the total weight of the cleaner.

One or more alkyl lactyllactates of the present technology can also be included in a dishwashing powder or gel in an amount of, for example, from about 0.01 to about 5% actives based on the total weight of the formulation.

One or more alkyl lactyllactates of the present technology can also be added into a carpet traffic spotter in an amount of, for example, from about 0.1% to about 8% actives, based on the total weight of the composition.

The following abbreviations may be used in the present application, especially in the examples:

SLES-2 or CS-230: Sodium lauryl 2 mole ether sulphate, available from Stepan Company as STEOL® CS-230 (26% active sodium laureth sulfate)

LMDO: Lauramidoproplyamine/Myristamidopropylamine oxide, available from Stepan Company as AMMONYX® LMDO (33% active)

HCG or CAPB: cocamidopropyl betaine, commercially available from Stepan Company as AMPHOSOL® HCG (31% active)

LL Lactyllactate

C12 LL or LLL or L3: Lauryl Lactyllactate, commercially available from Stepan Company under the trade name STEPAN-MILD® L3 (100% active)

C18 LL or SLL: Stearyl Lactyllactate

L2 Lauryl Lactate

NEODOL 25: C12-15 fatty alcohol (commercially available from Shell Oil Company under the trade name NEODOL® 25)

NEODOL 45: C14-15 fatty alcohol (commercially available from Shell Oil Company under the trade name NEODOL® 45)

NEODOL 67: C16-17 fatty alcohol (commercially available from Shell Oil Company under the trade name NEODOL® 67)

BRIJ 78: Polyoxyethylene (20) Stearyl Ether (commercially available from ICI Americas, Incorporated under the trade name BRIJ 78)

IPP: Isopropyl Palmitate, commercially available from HallStar Company, Chicago, Ill.

GMS: Glycerol Monostearate, commercially available from HallStar Company as HALLSTAR® GMS PURE (100% active)

Cetyl Alcohol: Cetyl Alcohol, also known as palmityl alcohol,

NaCl: Sodium Chloride

CMC: Critical Micelle Concentration

COMF: Cocamide Monoethanolamide (Cocamide MEA), commercially available from Stepan Company as NINOL® COMF (100% active)

SLS: Sodium Lauryl Sulfate, commercially available from Stepan Company as STEPANOL® WA-Extra (29% active)

DCFAS or SCS: Sodium Coco-Sulfate, commercially available from Stepan Company as STEPANOL® DCFAS (100% active)

SLL-FB: Sodium Lauroyl Lactylate, commercially available from Stepan Company as Stepan® SLL-FB CS-370: Sodium Laureth Sulfate, 3 EO, commercially available from Stepan Company as STEOL® CS-370 (70% active)

CS-270: Sodium Laureth Sulfate 2 EO, commercially available from Stepan Company as STEOL® CS-270 (70% active)

MES 16: Sodium Methyl-2-Sulfopalmitate/Disodium 2-Sulfopalmitate, commercially available from Stepan Company The presently described technology and its advantages will be better understood by reference to the following examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Viscosity Salt Response Test Method

The method used in the examples of the present application to measure viscosity salt responses of the compositions can be described as follows:
1. A desired surfactant composition is prepared and its pH is adjusted to about 5 to about 6.
2. The sample composition is poured off into a series of jars in the amount of about 100 grams of solution.
3. Different amount of dry sodium chloride is added into the solutions. The solutions are mixed well until the salt is fully dissolved.
4. The samples are centrifuged or sonicated and equilibrated to 25° C.
5. The viscosity of the sample is measured using a Brookfield Viscometer Helipath Stand (Brookfield Engineering Laboratories, Inc., Middleboro, Mass.) with a spindle 4 at speed 20.

Shake Foam Test Method

The method used in the examples of the present application to measure foaming performance of the compositions can be described as follows:
1. A 0.2% active sample solution is prepared in 25° C. tap water. A 0.2% solids solution is prepared if the active level is unknown.
2. 100.0 g+/−0.01 g, of the 0.2% sample solution is added to a 500 mL graduated cylinder. The initial foam is kept to a minimum.
3. 2.0 g+/−0.01 g of castor oil is added to the graduated cylinder, and a stopper is placed on the cylinder.
4. The graduated cylinder is placed in the shake foam machine, and the clamps are secured at the rubber stopper.
5. The shake foam machine is programmed to invert the cylinder 10 times.
6. The foam is allowed to settle for 15 seconds. A reading of total foam height, including the base of the 100 mL of solution, is taken.
7. After 5 minutes, foam height is read and recorded again as in Step 6.

Skin Feel Test Method

The skin feel test method may also be referred to as hand wash test method. A human in-vivo panel test method was used in the examples to evaluate body wash formulations. According to this method, hand wash tests are conducted using luke-warm (from about 95° F. to 105° F. or about 35° C.) tap water with a hardness of about, for example, 150 ppm (1.8/1 Ca:Mg). In the test, if the test product is a liquid body wash composition, 1 mL of the test product was dispensed to a panelist's wet palm. Panelists wash their hands by working the product into foam for 30 seconds followed by rinsing for 15 seconds. If the test product is a soap bar, panelists wet their hands with water; pre-wash their hands by making 5 half bar rotations in the palms of their hands; work their hands for 25 seconds to generate foam; and then rinse their hands for 15 seconds. The washing procedure is repeated one more time. Foam is collected in a graduated beaker and measured. Hands are rinsed under running water for 15 seconds and dried by paper towel. The panelists then rank test products for ease of application, wet stage and dry stage (skin-feel) performance properties on a scale from 1 to 5, with 1 being the worst, and 5 being the best.

The described human in-vivo panel test method can also be used to evaluate body wash formulations for a broad range of application, cleansing and skin feel properties. Panelists with normal, dry and moist skin type are selected for each test as determined using a NOVA moisture meter, commercially available from Nova Instruments, Incorporated. A NOVA reading less than 100 represents dry skin; a reading of 110-130 represents normal skin; and a reading of 130 or above represents moist skin. Panelists are asked to evaluate the experimental and control formulations using the procedure describe above. For example, in some experiments a 12% sodium 2 mole ether sulfate (SLES-2/CS-230) and 3% cocoamidopropyl betaine (CAPB/HCG) (which is believed to be the most widely used surfactant system in body washes) was used as the control. Experimental formulations tested may contain different amounts of surfactant actives (e.g., 12%, 13%, 14% or 15% by weight active) and may contain different ratios of primary surfactant to secondary surfactant (e.g., 4:1 or 14:1). A questionnaire was developed to record panelist's responses during and after body wash application.

According to the questionnaire, a panelist first needs to record the temperature and humidity of the environment, and his or her NOVA skin type. The panelist then needs to answer 14 questions as follows:
1. Ease of Application: 1=difficult; 5=easy
2. Flash Foam/Generation: 1=difficult; 5=easy
3. Bubble Size: 1=rich, creamy; 5=light, loose
4. Foam Volume: 1=virtually no foam; 5=copious amount of foam
5. Foam Feel: 1=non-lubricating; 5=very lubricating
6. Overall Impression: 1=bad; 5=good
7. Rinsability: 1=rinses poorly; 5=rinses easily and quickly
8. Wet Feel: 1=squeaky clean, 5=clean or substantive clean
9. Tackiness during drying: 1=tacky, sticky; 5=not tacky or sticky
10. Skin Tightness when dry: 1=very tight; 5 not tight
11. Skin Moisturizing: 1=very dry; 5=not dry
12. Skin Softness: 1=rough; 5=very soft
13. Overall Initial Impression: 1=bad; 5=good
14. Overall Impression After 2-3 Minutes: 1=bad; 5=good The data from the panelist assessment was recorded. In addition to panelist basic information, the questionnaire was structured in order to capture the panelist's responses related to product application, wet stage and dry stage. The panelists were asked to assess the performance of the experimental test sample/formulation and the control for each of the attributes shown here, with 1 being the worst and 5 being the best. As mentioned above, formulations with a variety of total active surfactant concentrations (e.g., 15% active) comprising different ratios of primary surfactants to secondary surfactants (e.g., 4:1 ratio) could be used. The pH of the formulation was adjusted to about 5 to about 6 using citric acid or sodium hydroxide. All experimental formulations were either compared to sodium 2 mole alcohol ether sulfate/cocamidopropyl betaine (CS-230/HCG) control or another control sample.

The difference in score between the experimental sample and the control was calculated for each property. The average score from the panelists was taken to determine the directional performance between the experimental sample and one control. If the overall differential score between the experimental sample and the control was positive, this indicated that the experimental sample performed directionally better than the control. If the overall differential score between the experimental body wash and the control is zero, the conclusion is that the experimental sample formulation performed equal to the control. If the difference between the experimental sample and control is negative, the conclusion is that the experimental sample performed inferior to the control.

Example 1

Preparation of Lauryl Lactyllactate at Room Temperature

Lauryl alcohol (19.2 g, 0.10 mol, LOROL® C 12/98, Cognis) was charged to a nitrogen flushed flask. L-lactide (14.4 g, 0.10 mol, Aldrich) was added as a solid and the mixture was stirred. One drop of sulfuric acid was added, and the slurry was stirred at room temperature for 3 days after which time a clear liquid resulted. NMR testing indicated complete conversion of the lactide. The resulting product was Lauryl lactyllactate (LLL or C12 LL), which is a mixture of C12-C14 lactyllactates.

Example 2

Preparation of C12-C18 Lactyllactate at an Elevated Temperature

C12-C18 alcohol (20.8 g, 0.10 mol, LOROL® Technisch, Cognis) was charged to a nitrogen flushed flask. L-lactide (14.4 g, 0.10 mol, Aldrich) was added as a solid, and the mixture was stirred. One drop of sulfuric acid was added; and the slurry was stirred at 50° C. for 20 hours after which time a clear liquid resulted. NMR testing indicated complete conversion of the lactide. The resulting product was a mixture of C12-C18 lactyllactates (C12-C18 LL).

Example 3

Viscosity Salt Response Tests for Compositions Using Alkyl Lactyllactates as Secondary Surfactants A series of compositions (5) were formulated, each of which contained 12% by weight active SLES-2 (CS-230) and 3% by weight active a secondary surfactant (4:1 ratio). The secondary surfactants were (1) HCG (control), (2) C12-C18 LL, (3) C16 LL, (4) C18 LL, and (5) C18 (Oleyl) LL.

Viscosity salt responses of these compositions were tested according to the viscosity salt response test method as describe above, and the results are shown in FIG. 1.

The results show that the compositions based on CS-230 as primary surfactant and C12-C18 LL, C18 (Oleyl) LL, C16 LL and C18 LL as secondary surfactants, increased viscosity in the presence of a proper amount of NaCl electrolyte. The results also show that the compositions based on CS-230 as primary surfactant with C12-C18 LL, C18 (Oleyl) LL and C16 LL as secondary surfactants, had higher viscosity values than the CS-230/HCG (control) compositions at lower concentrations of NaCl, while the compositions based on CS-230 and C18 LL had comparable viscosity values to the control compositions at low or higher concentrations of NaCl. Therefore, a lower amount of NaCl is needed for a composition based on CS-230 and C12-C18 LL, C18 (Oleyl) LL or C16 LL in order to have a desired viscosity in comparison to a composition based on CS-230 and HCG. By reducing the salt utilized in the production of the compositions of the present technology, the weight and corrosivity of such compositions are also reduced, thus leading to improved product handling and longer equipment life.

Example 4

Viscosity Salt Response Tests for Compositions Using Alkyl Lactyllactates as Secondary Surfactants A series of compositions (5) were prepared, each of which contains 12% by weight active SLES-2 (CS-230) and 3% by weight active a secondary surfactant (4:1 ratio). The secondary surfactants in this example were (1) HCG (control), (2) C12 LL, (3) NEODOL 25 LL, (4) NEODOL 45 LL, and (5) NEODOL 67 LL.

Figure 2:
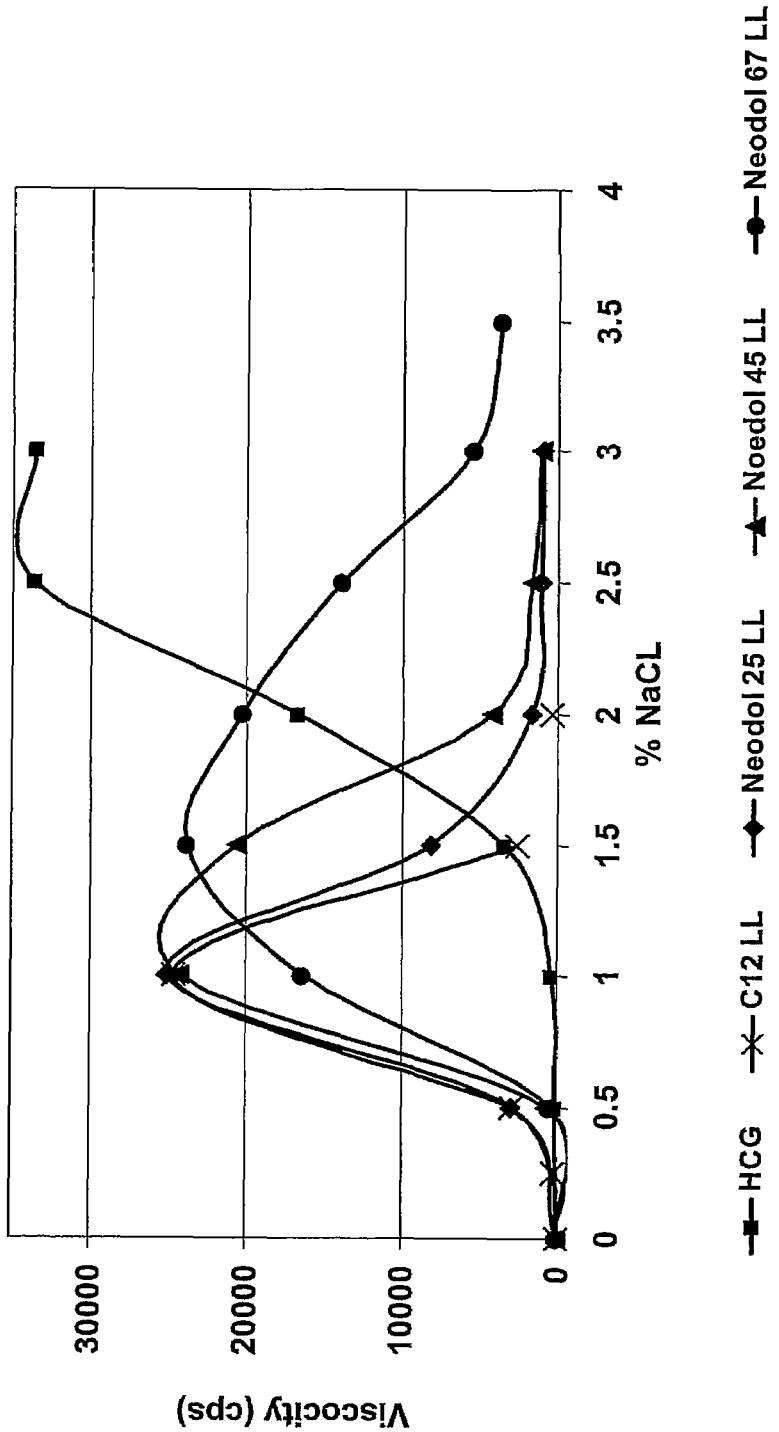

Viscosity salt responses of these compositions were tested according to the viscosity salt response test method as described above, and the results are shown in FIG. 2.

The results show that for 15% active compositions comprising CS-230 and LLL (4:1 ratio), there was an increase in viscosity with increase in the concentration of NaCl electrolyte until about 1% NaCl was used. The results also show that for 15% active composition of CS-230/LLL (4:1 ratio), comparable viscosity values can be achieved with significantly lower levels of NaCl electrolyte compared to a 15% active composition of CS-230/HCG (4:1 ratio). Similarly, the results show that when alkyl lactyllactates prepared from NEODOL 25, 45, and 67 are used, desirable viscosity values can be achieved with significantly lower levels of NaCl electrolyte compared to a composition based on CS-230 and HCG. As previously stated, reduction of the salt needed for a desirable viscosity value offers significant advantages associated with, for example, storage of the raw material itself and for production of consumer products in packaging equipment that is sensitive to corrosion. By reduction of the salt utilized to produce the compositions of the technology, the weight and corrosivity of such compositions are also reduced, thus leading to easier product handling and longer equipment life.

Example 5

Foaming Performance Tests for Compositions Using Alkyl Lactyllactates as Secondary Surfactants A series of six compositions were prepared, each of which contained 12% by weight active SLES-2 (CS-230) and 3% by weight active of a secondary surfactant (4:1 ratio). No oil was added to the compositions. The secondary surfactants were (1) HCG (control), (2) C12-C18 LL, (3) C16 LL, (4) C18 LL, (5) C18 (Oleyl) LL, and (6) C12 LL.

Figure 3:
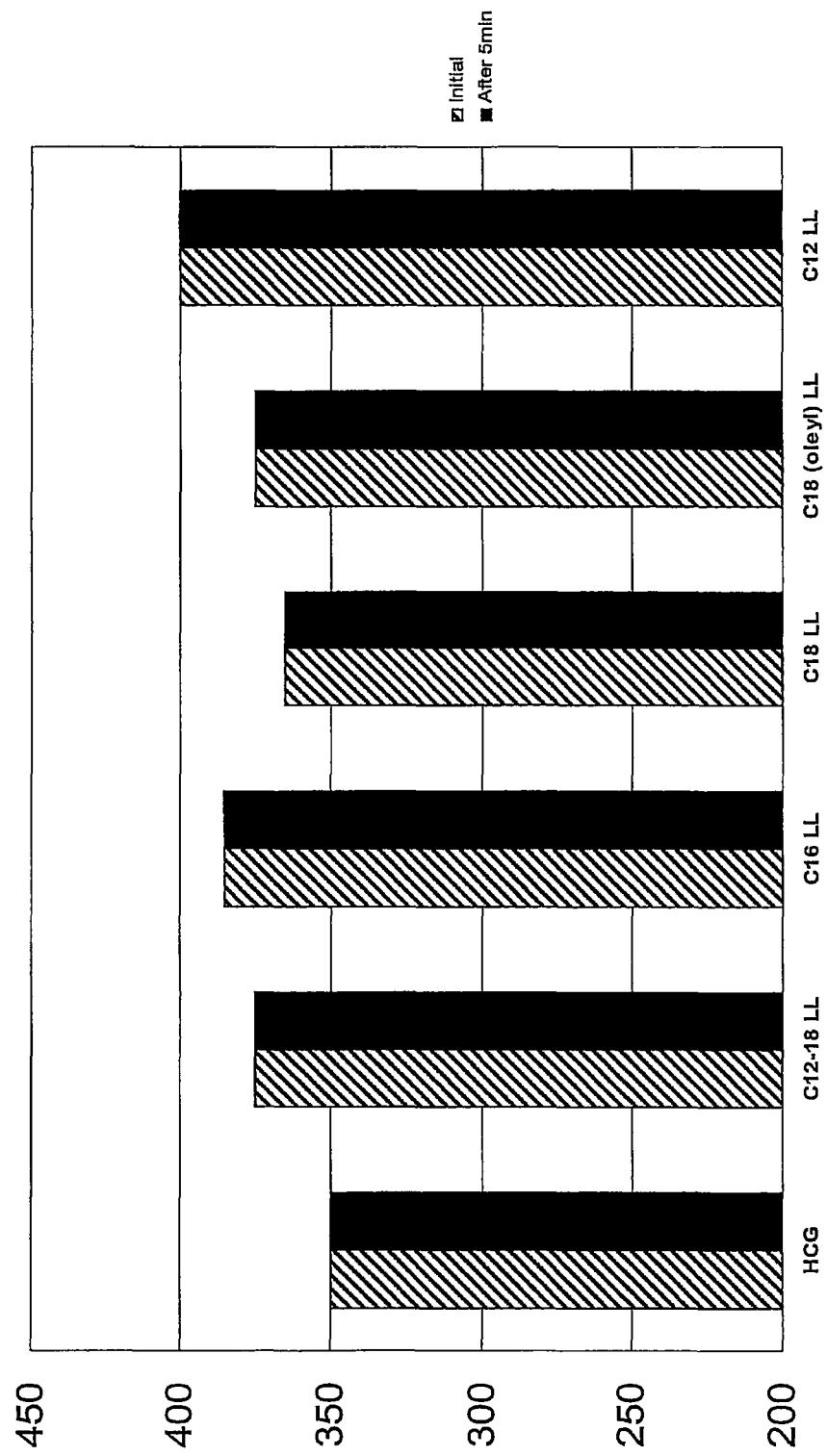
FIGS. 3 and 4 show the foam performance test (with no oil) results of exemplary compositions with or without alkyl lactyllactates of the present technology.

Foaming performance of each composition was tested by the shake foam test method (also called cylinder inversion test method) as described above. The foaming results of the six compositions without castor oil (both initial and after five minutes) were recorded and shown in FIG. 3.

The results without castor oil show that the experimental compositions based on CS-230 as primary surfactant and C12-C18 LL, C16 LL, C18 LL, C18 (Oleyl), and C12 LL as secondary surfactants have comparable or higher foam heights as compared to the CS-230/HCG (control) composition. The results also show that the CS-230/C12LL composition had the best overall performance among the alkyl lactyllactate compositions without castor oil tested in this example. Furthermore, this composition had significantly better foaming performance as compared to the CS-230/HCG control composition.

Experiments of compositions combined with castor oils were also performed. The results show that compositions based on CS-230 primary surfactant with C12-C18 LL, C16 LL and C12 LL secondary surfactants had comparable or better foaming performance as compared to the CS-230/HCG (control) composition in the presence of castor oils. Furthermore, the results show that the composition based on CS-230 with C16 LL had the best overall foaming performance in the presence of castor oil as compared to the CS-230/HCG (control) composition and the compositions containing CS-230 with the other alkyl lactyllactate secondary surfactants tested in this example. Lastly, the results show that the compositions containing C18 and C18 (oleyl) lactyllactates had the worst foaming performance in the presence of castor oil as compared to the compositions of other alkyl lactyllactates tested with the CS-230 primary surfactant and the CS-230/HCG (control) composition.

Example 6

Foaming Performance Tests for Compositions Using Alkyl Lactyllactates as Secondary Surfactants A series of five compositions were prepared, each of which contained 12% by weight active SLES-2 (CS-230) and 3% by weight active a secondary surfactant (4:1 ratio). No oil was added to the compositions. The secondary surfactants were (1) HCG (control), (2) C12 LL, (3) NEODOL 25 LL, (4) NEODOL 45 LL, and (5) NEODOL 67 LL.

Figure 4:
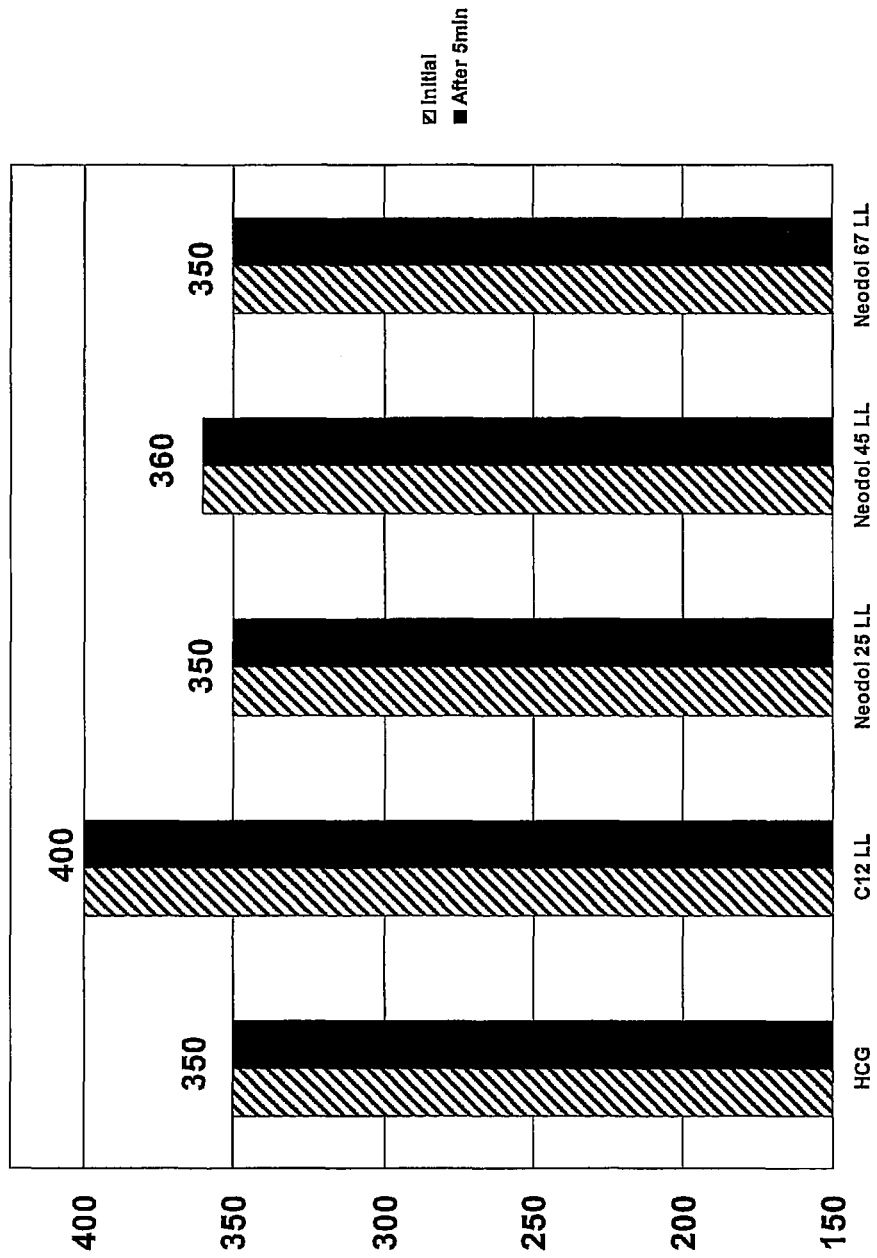

Foaming performance of each composition was tested by the shake foam test method as described above. The foaming results of the five compositions without castor oil (both initial and after five minutes) are shown in FIG. 4.

The results show that the composition based on CS-230 and C12 LL has better foaming performance than the CS-230/HCG (control) composition without the addition of castor oil. The results also show that compositions containing alkyl lactyllactates prepared from NEODOL 25, 45, and 67 and CS-230 had comparable foaming performance as compared to the CS-230/HCG (control) composition without the addition of castor oil.

Experiments of compositions with the addition of castor oils were also performed. The results show that compositions containing the alkyl lactyllactates prepared from NEODOL 25, 45, and 67 and CS-230 had comparable performance with each other, and each of them had directionally inferior (i.e., slightly poorer) foaming performance as compared to the CS-230/HCG (control) composition in the presence of castor oil. The composition based on CS-230 and C12 LL still showed substantially better foaming performance than the CS-130/HCG (control) composition in the presence of castor oil. The results also show that the presence of a citric acid/sodium citrate buffer did not have a significant effect on the foaming performance of the composition containing CS-230 and C12 LL with or without castor oil.

Example 7

Softness and Moisturization Performance Comparison Between Compositions Based on Alkyl Lactyllactates and HCG A series of five body wash compositions were prepared, each of which contained 12% by weight active SLES-2 (CS- 230) and 3% by weight active a secondary surfactant (4:1 ratio). The secondary surfactants were (1) HCG (used as a control), (2) C12 LL, (3) C16 Lactylate, (4) Oleyl LL, and (5) C12-18 LL.

Figure 5:
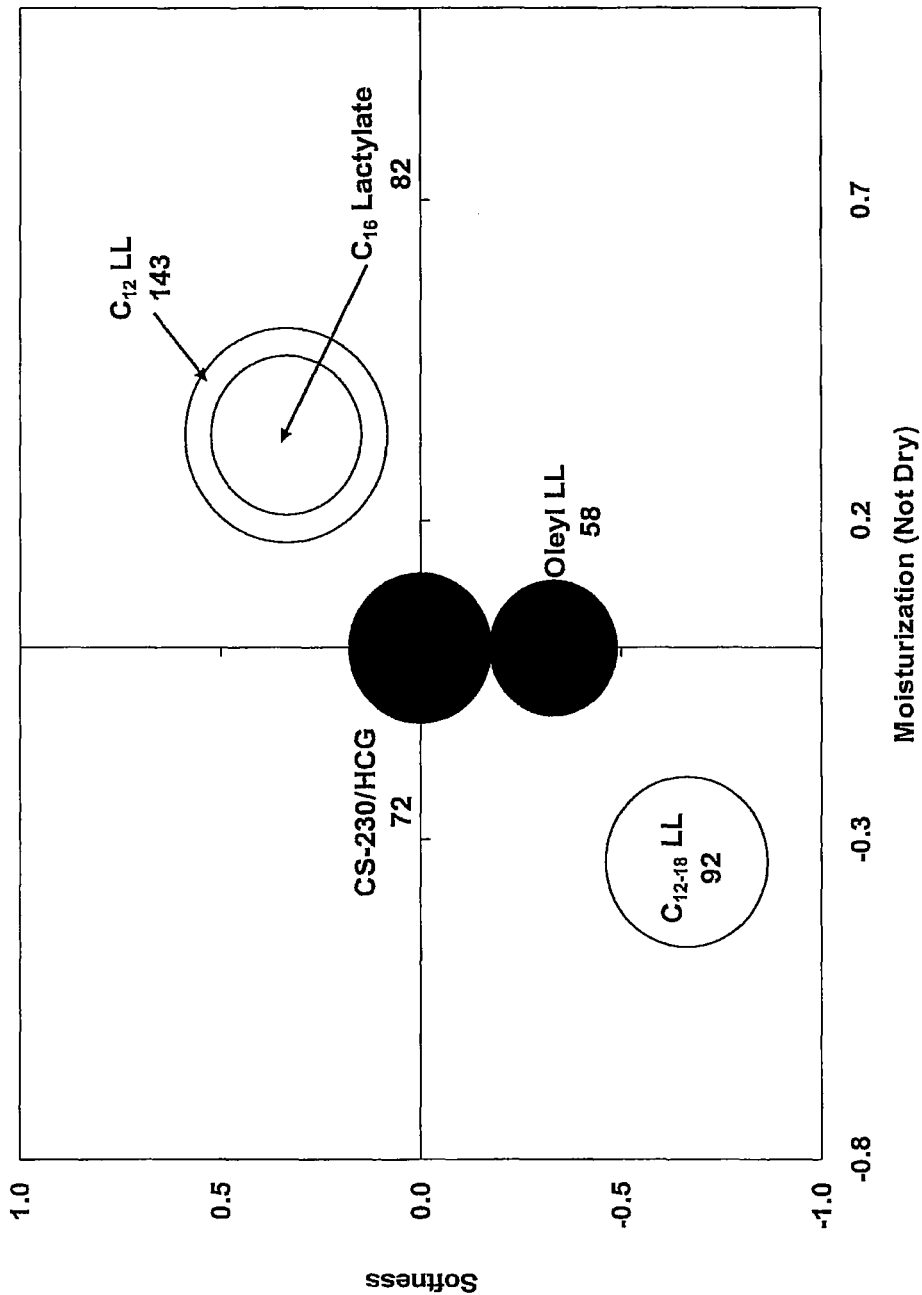
FIGS. 5 and 6 show the body wash performance comparison of exemplary compositions with or without alkyl lactyllactates of the present technology.

Softness and moisturization performance of each composition were tested using the skin feel test method as described above. The relative results of them as compared to the composition containing HCG/CS-230 (control) are shown in FIG. 5.

The results show that the compositions based on CS-230/C12 LL and CS-230/C16 Lactylate had better softness and moisturization performance as compared to the CS-230/HCG (control) composition and the compositions based on CS-230/C18 (Oleyl) LL and CS-230/C12-C18 LL.

Example 8

Softness and Moisturization Performance Comparison of Body Washes with NEODOL 25 LL, NEODOL 45 LL, NEODOL 67 LL and LLL Against Body Wash with HCG Five body wash compositions were prepared, each of which contained 12% by weight active SLES-2 (CS-230) and 3% by weight active a secondary surfactant (4:1 ratio). The secondary surfactants were (1) HCG (control), (2) LLL (i.e., C12 LL), (3) NEODOL 25 LL, (4) NEODOL 45 LL, and (5) NEODOL 67 LL.

Figure 6:
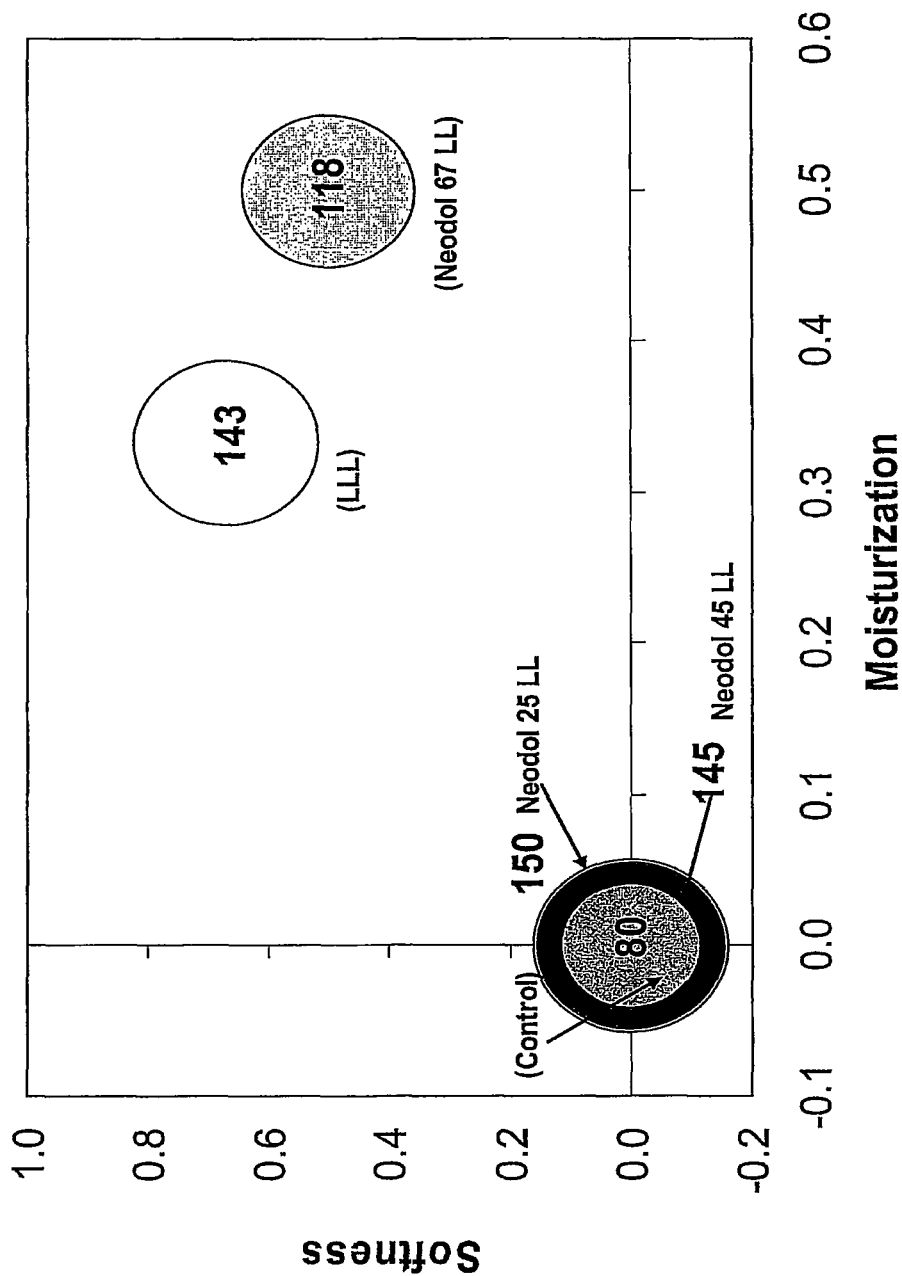

Softness and moisturization performance of each composition during body wash were tested by the skin feel test method as described above. The relative results as compared to the composition containing HCG/CS-230 (control) are shown in FIG. 6.

The results show that compositions containing CS-230/LLL and CS-230/NEODOL 67 LL had better softness and moisturization performance as compared to the CS-230/HCG (control) composition. The compositions based on CS-230/NEODOL 25 LL and CS-230/NEODOL 45 LL had comparable softness and moisturization performance compared to the CS-230/HCG (control) composition.

Example 9

Comparative Study of the Stability of LLL Formulations with and without a Buffer Two LLL compositions were formulated, one with a buffer, and the other without. The buffer used was a 0.5% active sodium citrate/citric acid and 0.5% active ammonium lactate/lactic acid system.

The stability of the two compositions were studied at both room temperature and at 50° C. over a four week time period. The results in terms of pH values and viscosities of the two compositions are recorded in FIG. 7.

The results show that the CS-230/LLL composition with the buffer of 0.5% active sodium citrate/citric acid and 0.5% active ammonium lactate/lactic acid had a more stable pH and viscosity at 50° C. over the four week period as compared to the same composition without a buffer.

Example 10

Comparative Study of Stearyl Lactyllactate as a Co-Emulsifier in Oil-in-Water Emulsions Two oil-in-water (O/W) emulsions A and B were prepared in this example as their formulations shown in the table below.

TABLE 1

| Ingredients | Formulation A Wt % Active | Formulation B (Control) Wt % Active |
|---|---|---|
| Deionized (D.I.) Water | Q.S. to 100 | Q.S. to 100 |
| BRIJ 78 | 1.0 | 1.0 |
| Stearyl Lactyllactate | 1.5 | 0 |
| IPP | 10.0 | 10.0 |
| GMS | 1.5 | 1.5 |
| Cetyl Alcohol | 2.0 | 2.0 |
| Preservative | q.s. | q.s. |
| Initial viscosity @ 25° C. (cps) | 7,200 | 6,000 |
| Viscosity after 3 days @ 25° C. (cps) | 8,600 | 6,000 |

The difference between the two emulsions is that emulsion A contained 1.5 wt % of stearyl lactyllactate (SLL), and the control emulsion B did not. The viscosities of the two compositions (both initial and after 3 days) were measured and recorded in the table above.

The results show that stearyl lactyllactate increased the viscosity of oil-in-water emulsions. Such an outcome allows for the production of final products utilizing such alkyl lactyllactates in a more cost effective and cost efficient manner due to lower amounts of such components being utilized.

Example 11

Preparation of Palmityl Lactyllactate

Palmityl alcohol (24.2 g, 0.10 mol, LOROL® C 14/98, Cognis) was charged to a nitrogen flushed flask. L-lactide (14.4 g, 0.10 mol, Aldrich) was added as a solid, and the mixture was stirred. One drop of sulfuric acid was added, and the slurry was stirred at about 35° C. for approximately 30 hours after which time a clear liquid resulted. NMR test indicates complete conversion of the lactide. The resultant product was palmityl lactyllactate (C 16 LL).

Example 12

Preparation of Oleyl Lactyllactate

Oleyl alcohol (26.7 g, 0.10 mol, HD Ocenol® 90/95V, Cognis) was charged to a nitrogen flushed flask. L-lactide (14.4 g, 0.10 mol, Aldrich) was added as a solid, and the mixture is stirred. Two drops of sulfuric acid was added, and the slurry was stirred at about 50° C. for approximately 20 hours after which time a clear liquid resulted. NMR test indicated complete conversion of the lactide. The resultant product was oleyl lactyllactate (C18 (oleyl) LL).

Example 13

Preparation of Isostearyl Lactyllactate

Isostearyl alcohol (13.1 g, 0.05 mol, Jarchem Industries, Inc., Newark, N.J.) was charged to a nitrogen flushed flask. L-lactide (7.5 g, 0.05 mol, Aldrich) was added as a solid, and the mixture was stirred. One drop of sulfuric acid was added, and the slurry stirred at about 50° C. for approximately 16 hours after which time a clear liquid resulted. NMR test indicated complete conversion of lactide. The resultant product was isostearyl lactyllactate (C18 (isostearyl) LL).

Example 14

Softness and Moisturization Performance Tests of Compositions of Different Total Actives A series of five body wash compositions were prepared. The control composition contained 12% by weight active SLES-2 (CS-230) and 3% by weight active CAPB (HCG) (4:1 ratio). The other four body wash compositions contained SLES-2 and the C12 LL of the present technology in an active weight ratio of 14:1. The amounts of total actives in the four compositions are 15%, 14%, 13%, and 12% by weight, respectively.

Figure 8:
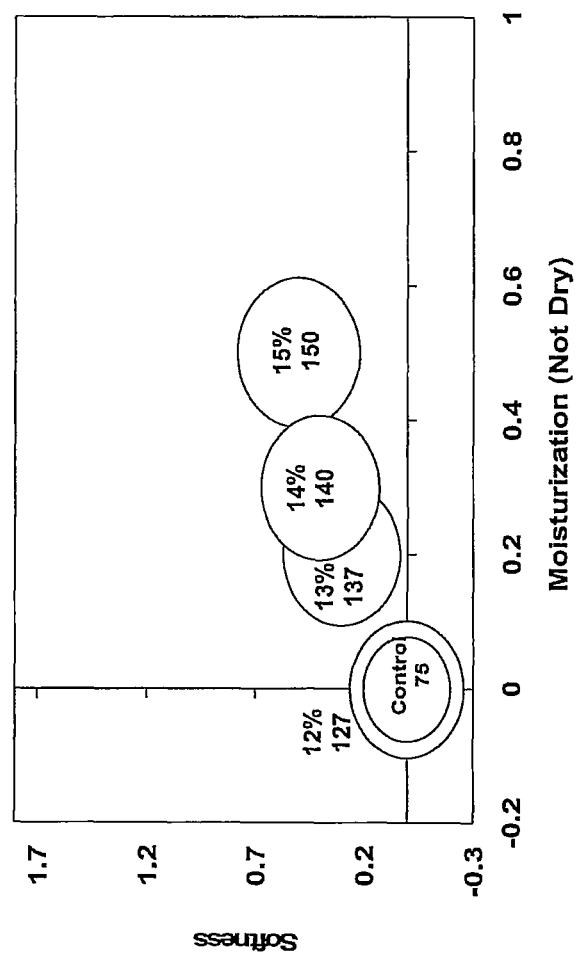
FIG. 8 shows the hand wash test results of exemplary compositions with lauryl lactyllactate of the present technology at different total active concentrations as compared to a control composition without lauryl lactyllactate ("LLL" or "L3") of the present technology.

Softness and moisturization performance of each composition was tested using the skin feel test method as described above. The relative results of a three-panelist test as compared to the control composition are shown in FIG. 8.

The results show that the compositions based on CS-230 and C12 LL in a 14:1 ratio and containing total actives in the amount of 15%, 14%, and 13% all exhibited better softness and moisturization performance and higher foaming (i.e., foam height) than the CS-230/HCG (control) composition (which contains a total of 15% actives in a 4:1 ratio). The composition of the present technology that contained a total of 12% active of CS-230 and C12 LL in a 14:1 ratio showed comparable softness and moisturization performance and higher foaming as compared to the CS-230/HCG (control) composition. The results illustrate that a reduced amount of C12 LL is required to achieve comparable softness, moisturization, and foam height than when CAPB is used. The results also show that a lesser amount of total actives is needed for a body wash composition in order to achieve a performance comparable to that of a composition based on SLES-2 and CAPB. This can reduce cost, lower weight of a final product, and make the body wash product of the present technology more environmentally friendly.

Example 15

Comparative Viscosity Salt Response Tests for Compositions Using Lauryl Lactyllactate or Cocamidopropyl Betaine as Secondary Surfactants A series of five body compositions (5) were formulated. Two of the compositions contained 12% by weight active of SLES-2 (CS-230) as the primary surfactant and 3% by weight active of CAPB or C12 LL as the secondary surfactant (4:1 ratio). Two other compositions contained 14% by weight active of SLES-2 and 1% by weight active of CAPB or C12 LL (14:1 ratio). The last composition contained 15% by weight active of SLES-2 and no secondary surfactant.

Figure 9:
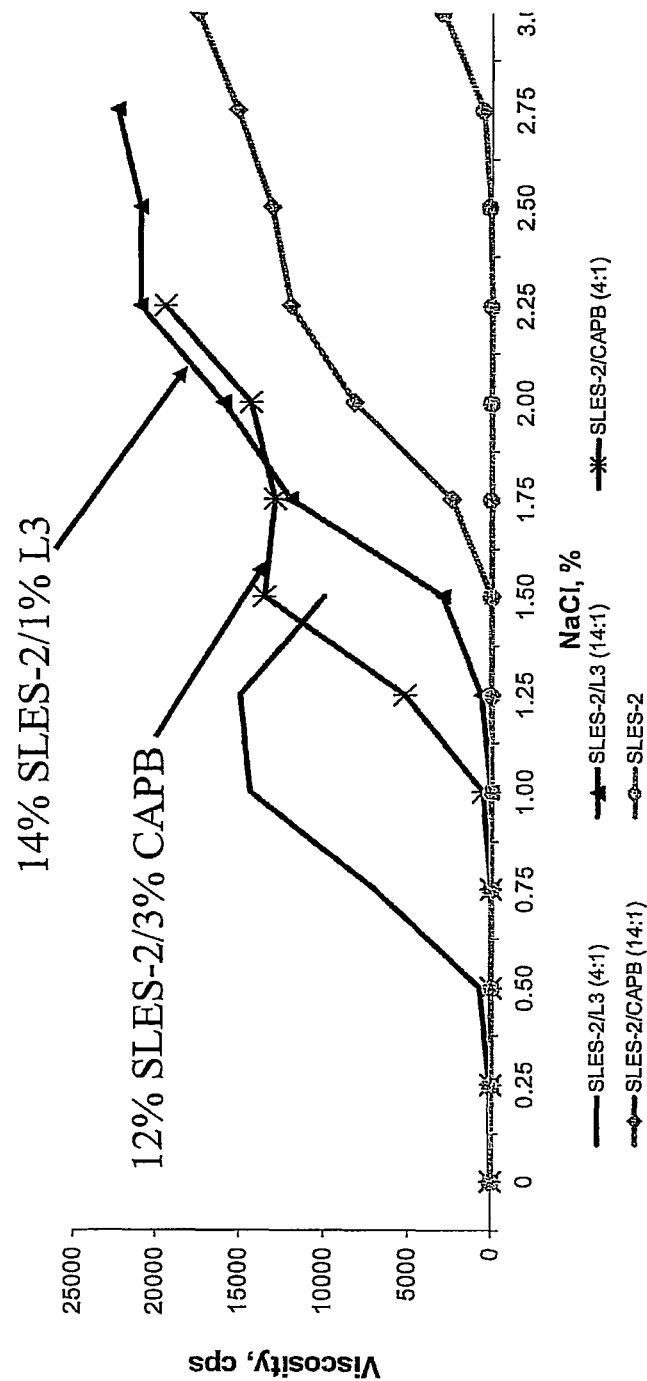
FIG. 9 shows viscosity salt response curves of four compositions containing a primary surfactant and a secondary surfactant at a 4:1 or 14:1 ratio. The total active amount of surfactants is 15% in each composition. The primary surfactant used is sodium lauryl 2 mole ether sulphate (SLES-2 or CS-230). The secondary surfactant used is cocamidopropyl betaine (CAPB or HCG) or L3.

Viscosity salt responses of these compositions were tested according to the viscosity salt response test method as describe above, and the results are shown in FIG. 9.

The results show that when no secondary surfactant was used, the viscosity of the 15% active composition of SLES-2 remained almost water thin (i.e., having a viscosity similar to water and is about 1 cps at 25° C.) even when 2.5% by weight of NaCl electrolyte was used. The compositions containing CAPB or C12 LL secondary surfactant, on the other hand, built up viscosity in the presence of a proper amount of NaCl electrolyte. The results also show that the composition based on SLES-2 and C12 LL at a 4:1 ratio had higher viscosity values than the SLES-2/CAPB compositions of the same ratio at lower concentrations of NaCl, while the composition based on SLES-2 and C12 LL at a 14:1 ratio had higher viscosity values than the SLES-2/CAPB compositions of the same ratio at low or higher concentrations of NaCl. Therefore, as shown in FIG. 9, if the desired viscosity of a body wash composition is lower than 15000 cps, a much lower amount of NaCl is needed for a composition based on SLES-2 and C12 LL, in order to reach the desired viscosity, in comparison to a composition based on SLES-2 and CAPB. By reducing the salt utilized to produce the compositions of the technology, the corrosivity of such compositions are also reduced, thus leading to, at least, easier product handling and longer equipment life.

In addition, the results unexpectedly show that the composition containing 1% by weight active of C12 LL and 14% by weight active of SLES-2 had higher or compatible viscosity values as compared to the composition containing 3% by weight active of CAPB and 12% by weight active of SLES-2, when the amount of NaCl used was 1.75% or higher. Therefore, when the desired viscosity of the composition of a body wash composition is higher than 15000 cps, a lower amount of the secondary surfactant is needed to reach the desired viscosity using the same amount of NaCl when the secondary surfactant used is C 12 LL rather than CAPB.

Example 16

Hand Foaming and Skin Feel Tests of Soap Bars

In this example, three soap bar samples were tested. Sample A (control) was a re-stamped commercially available soap bar. Sample B was a commercial soap bar re-processed with 2% by weight of lauryl lactyllactate (L3) and restamped. Sample C was made from scratch using 80/20 tallow/coco soap base, 2% palm stearin free fatty acid (FFA), 4% betaine, 2% L3, and 2% a mixture of sodium methyl 2-sulfolaurate and disodium 2-sulfolaurate (commercially available from Stepan Company as ALPHA-STEP® BSS-45). Compared to the commercially available soap bar (Sample A), Sample C contains 2% palm stearin FFA instead of 5-6% found in Sample A and contains 2% L3.

Figure 10:
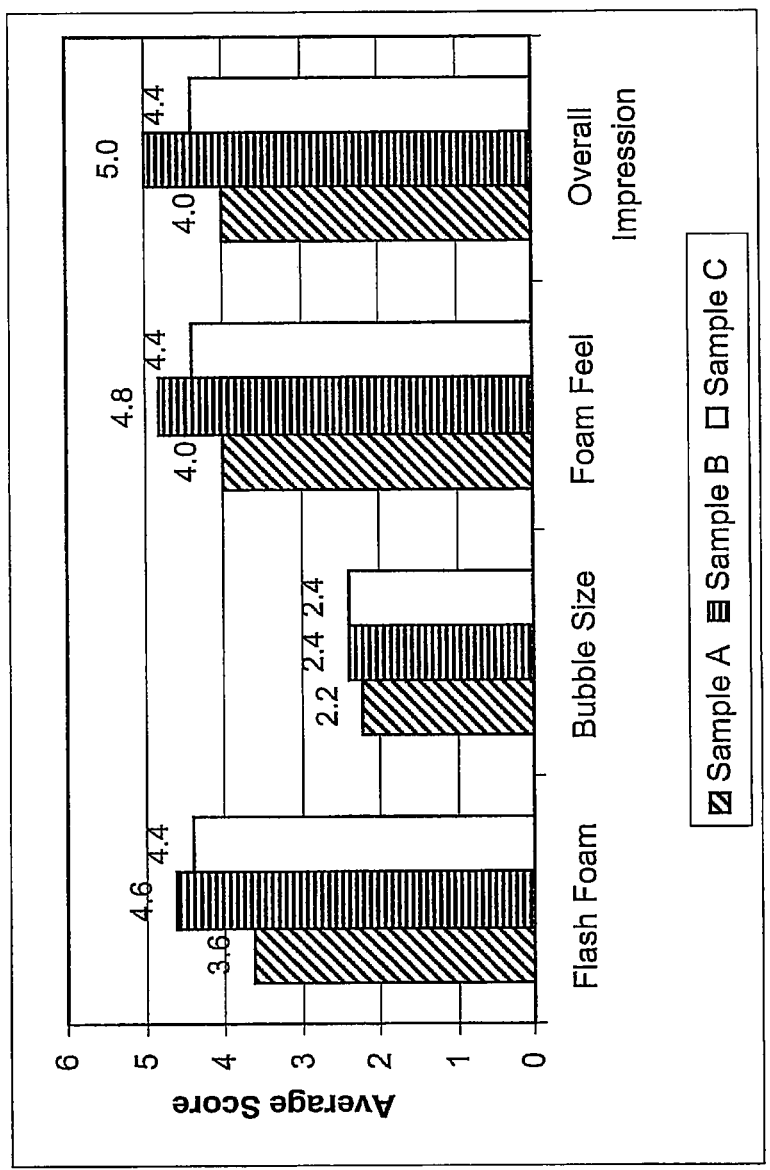
FIG. 10 shows the expert panel hand wash study results of three soap samples.
Figure 11:
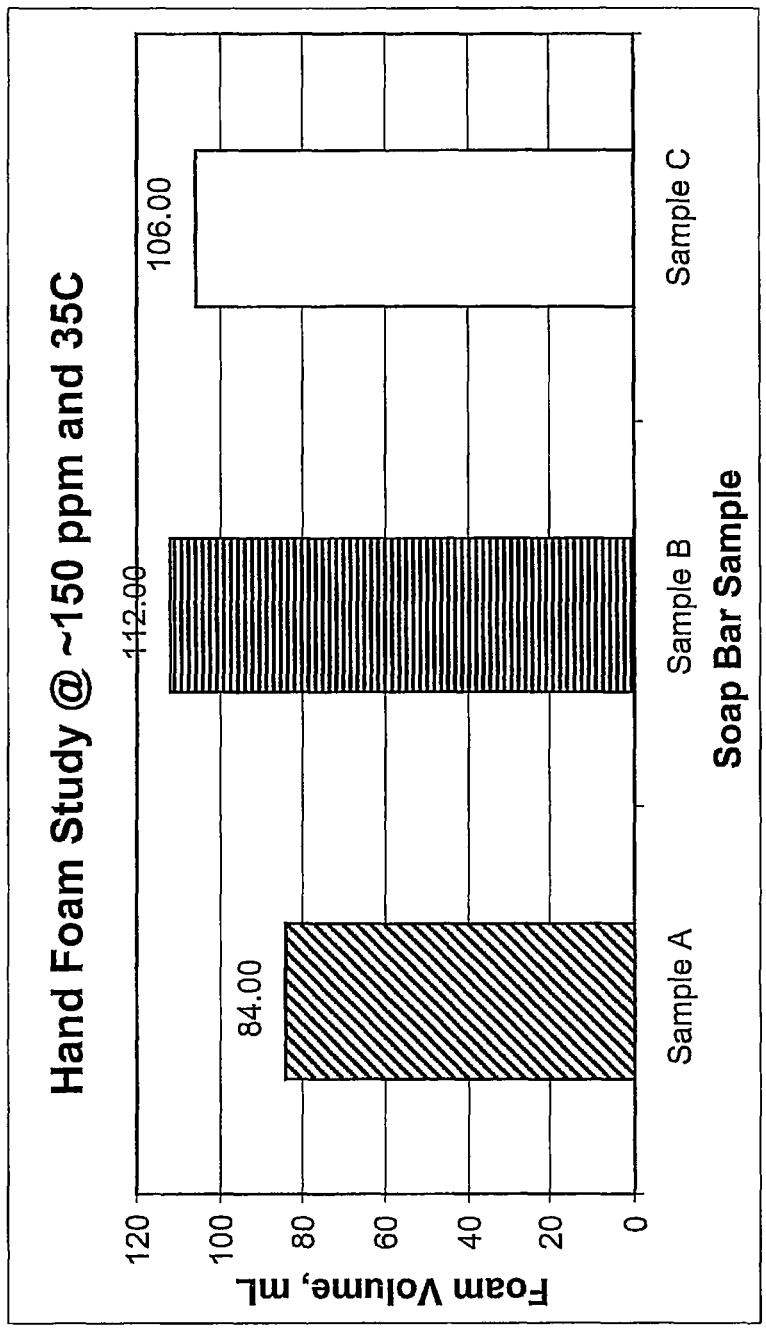
FIGS. 11 and 12 show the hand foaming test results of three soap samples.
Figure 12:
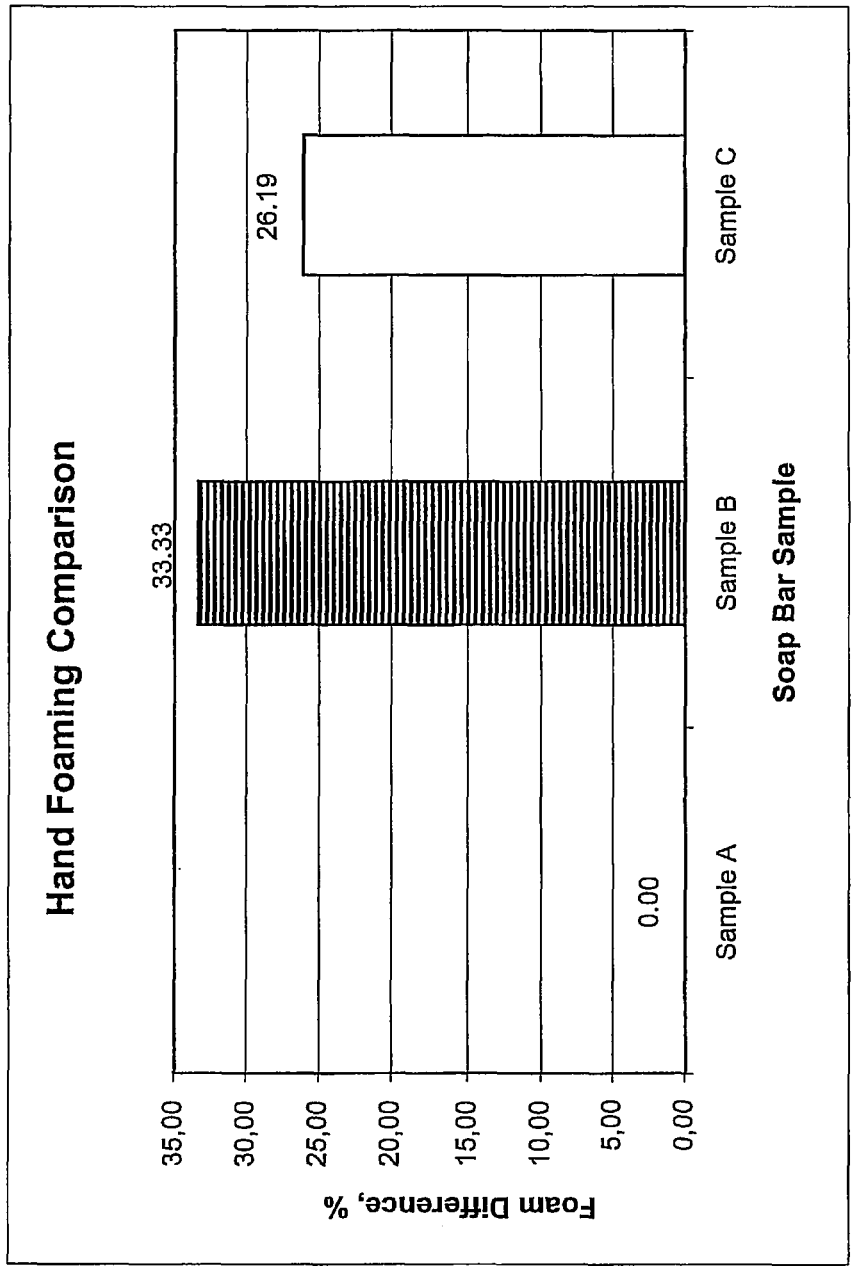

Hand foaming and skin feel tests of each composition were conducted using the skin feel test method as described above. The various comparative hand foaming results are shown in FIGS. 10-12, and the various comparative skin feel results are shown in FIGS. 13-14.

Figure 13:
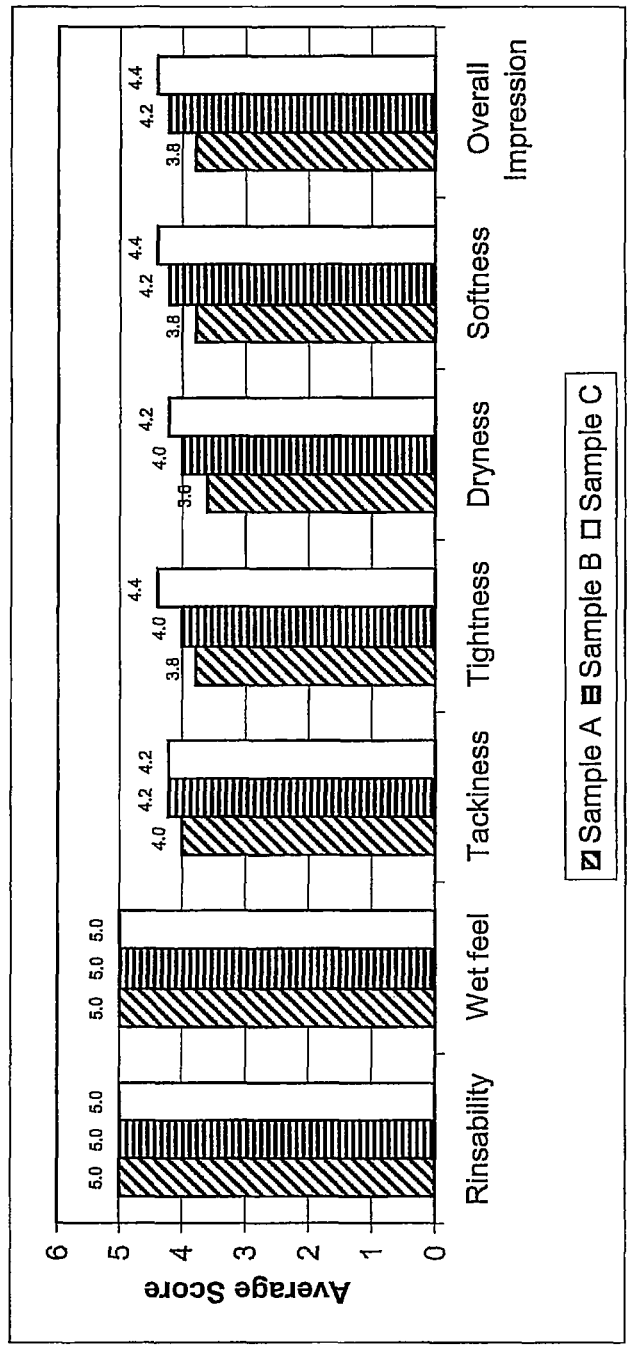
FIGS. 13 and 14 show the expert panel skin feel test results of three soap samples.
Figure 14:
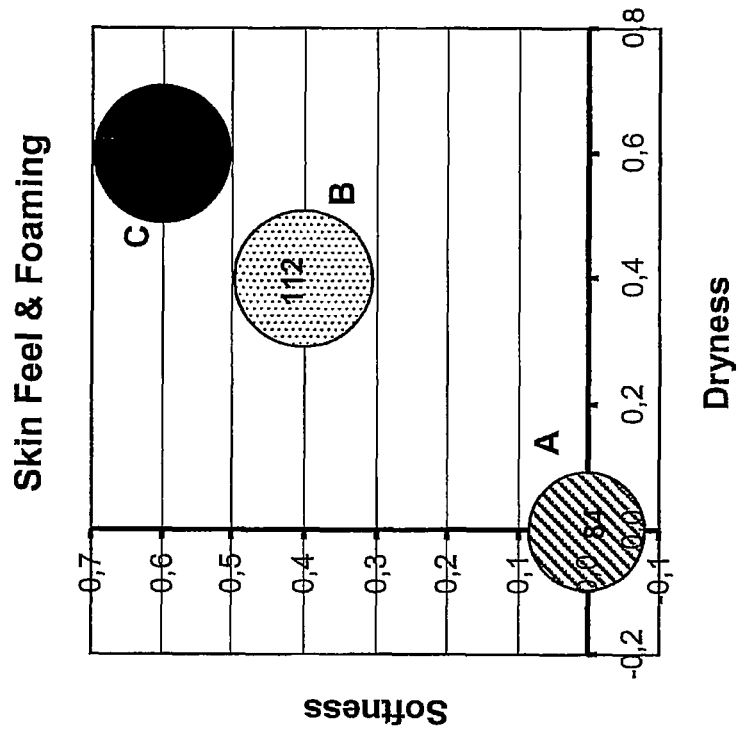

In FIG. 13, "rinsability" means the ability of the product to be easily removed after application; "wet feel" means the ability of the product to leave squeaky clean, clean or substantive after feel; "tackiness" means the perception of stickiness on skin during wet or dry transition; "tightness" means the extent of pulling on the skin after drying; "dryness" means the extent the skin feels dehydrated with flaking and scaling; and "softness" means a pleasant silky feel on the skin.

The results show that adding L3 to a commercial soap bar delivered significant improvement in foaming performance and some improvement (i.e, directional improvement) in most skin feel attributes. It was found that L3 did not affect the rinsability and wet feel properties of the commercial soap bar. Also, the reduced concentration of FFA in Sample C did not negatively impact the physical properties of the bar. Further, during processing of Sample C, it was observed that L3 improved the plasticity of the bar, which suggests a positive impact on preventing the bar from cracking.

Example 17

Comparative Viscosity Salt Response and Hand Foam Studies of Different Primary Surfactants Three body wash compositions comprising three different primary surfactants, and lauryl lactyllactate (L3) of the present technology as secondary surfactant in a 14:1 active ratio, were formulated. The formulations of the three compositions are shown in the table below.

TABLE 2

Compositions Containing Different Primary Surfactants

| Ingredients | Wt. % Active | | |
|---|---|---|---|
| Sodium Lauryl Ether Sulfate | 14.0 | | |
| Sodium Lauryl Sulfate | | 14.0 | |
| Sodium Coco-Sulfate | | | 14.0 |
| Lauryl Lactyllactate | 1.0 | 1.0 | 1.0 |
| Water (deionized) | 45.0 | 50.0 | 85.0 |
| Citric Acid | Q.S. | Q.S. | Q.S. |
| Appearance | Clear | Clear | Clear |
| pH | 5.8 | 5.8 | 5.7 |

A composition containing 12% by weight active SLES-2 (CS-230) and 3% by weight active CAPB (HCG) (4:1 ratio) was used as a control. Three comparative compositions containing CAPB (HCG) as the secondary surfactant in lieu of L3, but otherwise having identical formulations as those shown in Table 2, were also prepared.

Figure 15:
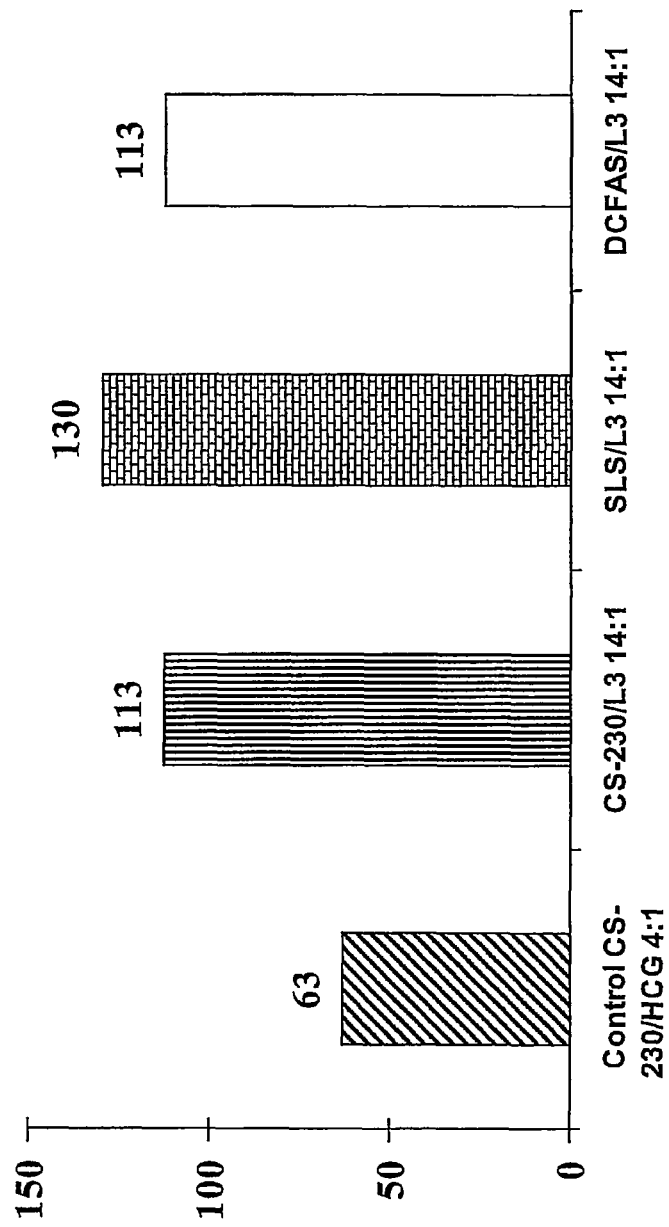
FIG. 15 shows the hand foaming test results of three compositions comprising three different primary surfactants and L3 as compared to a control composition comprising CS-230 and HCG.
Figure 16:
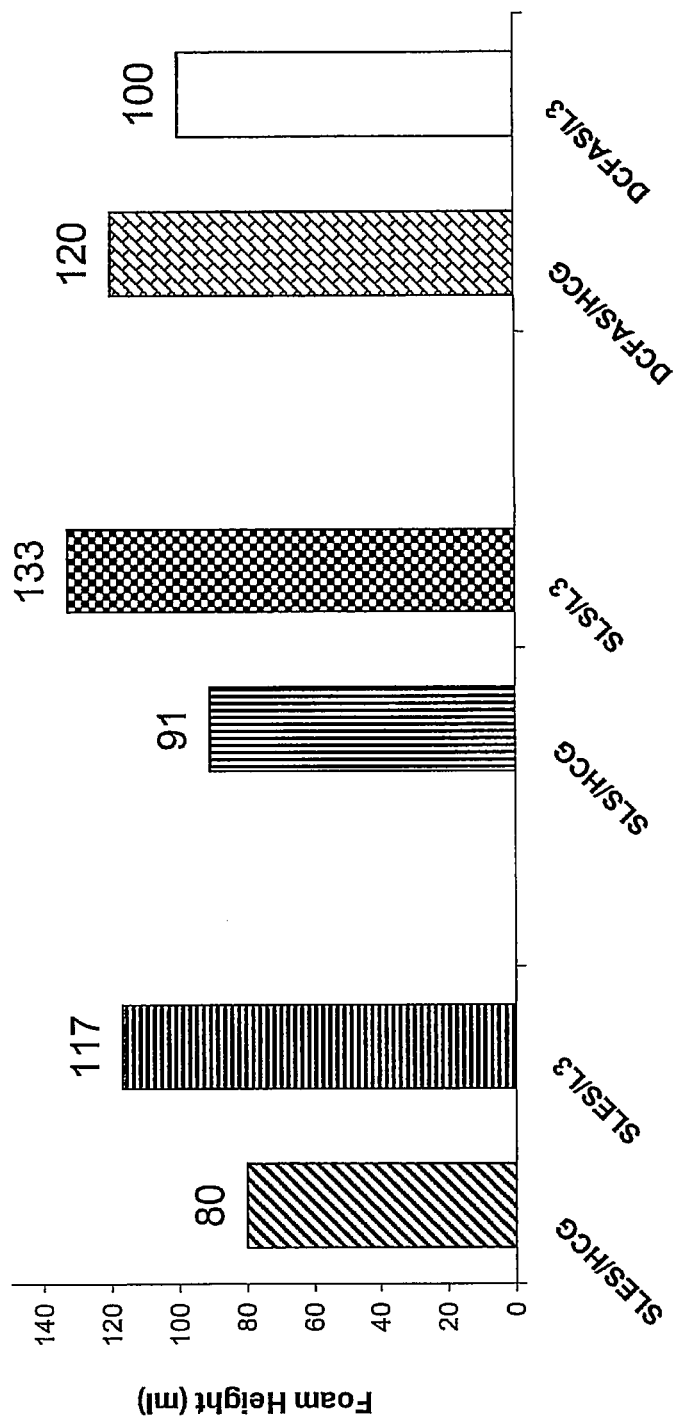
FIG. 16 shows the hand foaming test results of three compositions comprising three different primary surfactants and L3 as compared to three compositions comprising the three different primary surfactants and HCG.

Hand foaming tests of the three compositions of the present technology were first conducted against the CS-230/HCG (control) composition using the skin feel test method as described above. The comparative hand foaming results are recorded in FIG. 15. The three compositions of the present technology were then studied relative to their respective comparative composition using the skin feel test method as described above. The hand foaming results are shown in FIG. 16.

The results show that the three compositions containing SLES-2, SLS, or SCS (DCFAS) as primary surfactant and L3 as secondary surfactant all exhibited better hand foam performance than the CS-230/HCG (control) composition. The compositions containing 14.0% by weight active SLES-2 or SLS and 1.0% by weight active L3 had better hand foam performance than the respective comparative composition containing 14% by weight active SLES-2 or SLS and 1.0% by weight active HCG.

Figure 17:
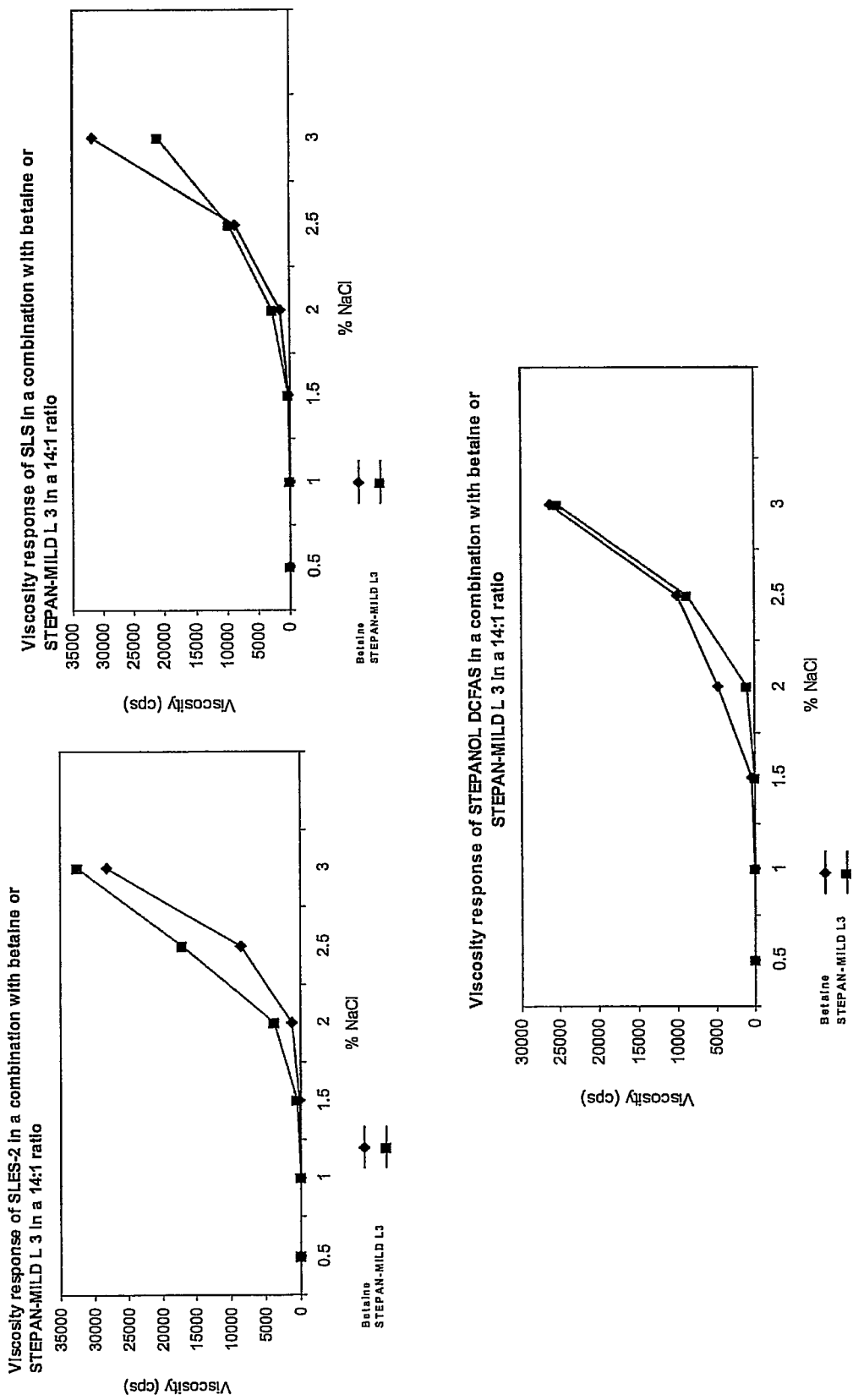
FIG. 17 shows the viscosity salt response curves of three compositions comprising three different primary surfactants and L3 as compared to three compositions comprising the three different primary surfactants and HCG.

Viscosity salt responses of the compositions of the present technology using L3 as the secondary surfactant, and the comparative compositions using HCG (a betaine) as the secondary surfactant, were tested according to the viscosity salt response test method as describe above. The results are shown in FIG. 17.

Example 18

Comparative Hand Foaming Studies of Compositions Containing Different Secondary Surfactants In this example, a series of six (6) compositions were prepared for hand wash foaming tests. The formulations of the 6 compositions were as follows:
1. CS-230/HCG (control): containing 12% by weight active SLES-2 (CS-230) and 3% by weight active CAPB (HCG) (4:1 ratio);
2. CS-230/L3,12% active: containing 12% by weight total active of CS-230 and L3 in a 14:1 ratio;
3. CS-230/L3, 15% active: containing 14% by weight active CS-230 and 1% by weight active L3 (14:1 ratio);
4. CS-230/Amide: containing 14% by weight active CS-230 and 1% by weight active COMF (cocamide monoethanolamide) (14:1 ratio);
5. CS-230/Amphoacetate: containing 14% by weight active CS-230 and 1% by weight active sodium lauryl amphoacetate ("am") (14:1 ratio);
6. CS-230/Sulfosuccinate: containing 14% by weight active CS-230 and 1% by weight active sodium lauryl sulfosuccinate ("ss") (14:1 ratio).

Figure 18:
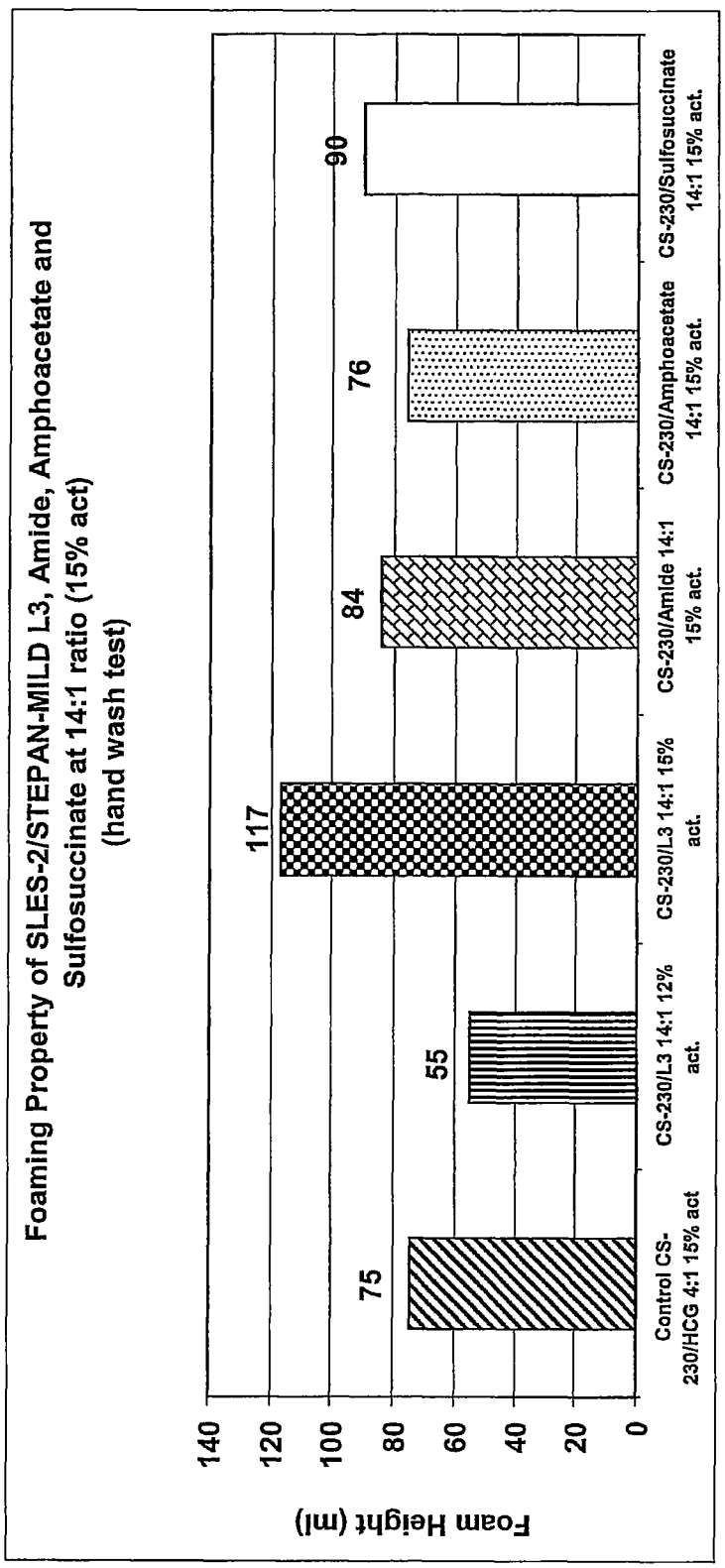
FIGS. 18-20 show hand wash foaming results of three series of compositions comprising SLES-2 (CS-230) as the primary surfactant and, HCG, L3, cocamide monoethanolamide, amphoacetate, sulfosuccinate, or a combination thereof as the secondary surfactant.

Hand foaming tests of the 6 compositions were conducted using the skin feel test method (also called hand wash test method) as described above. The comparative hand foaming results are recorded in FIG. 18.

The results show that L3 of the presently described technology had substantially better hand foaming performance than HCG, amphoacetate and sulfosuccinate when they are used to formulate body wash compositions.

Example 19

Comparative Hand Foaming Studies of Compositions Containing HCG, L3 Amphoacetate, and/or Sulfosuccinate In this example, a series of six (6) compositions were prepared for hand wash foaming tests. The formulations of the 6 compositions were as follows:
1. CS/HCG (control): containing 12% by weight active SLES-2 (CS-230) and 3% by weight active CAPB (HCG) (4:1 ratio);
2. CS/L3 (4:1): containing 12% by weight active CS-230 and 3% by weight active L3 (4:1 ratio);
3. CS/L3 (14:1): containing 14% by weight active CS-230 and 1% by weight active L3 (14:1 ratio);
4. CS/HCG/L3: containing 12% by weight active CS-230 and 3% by weight active a secondary surfactant (4:1 ratio), wherein the secondary surfactant comprises HCG and L3 in a 1:1 ratio;
5. CS/HCG/am: containing 12% by weight active CS-230 and 3% by weight active a secondary surfactant (4:1 ratio), wherein the secondary surfactant comprises HCG and sodium lauryl amphoacetate ("am") in a 1:1 ratio;
6. CS/HCG/ss: containing 12% by weight active CS-230 and 3% by weight active a secondary surfactant (4:1 ratio), wherein the secondary surfactant comprises HCG and sodium lauryl sulfosuccinate ("ss") in a 1:1 ratio.

Figure 19:
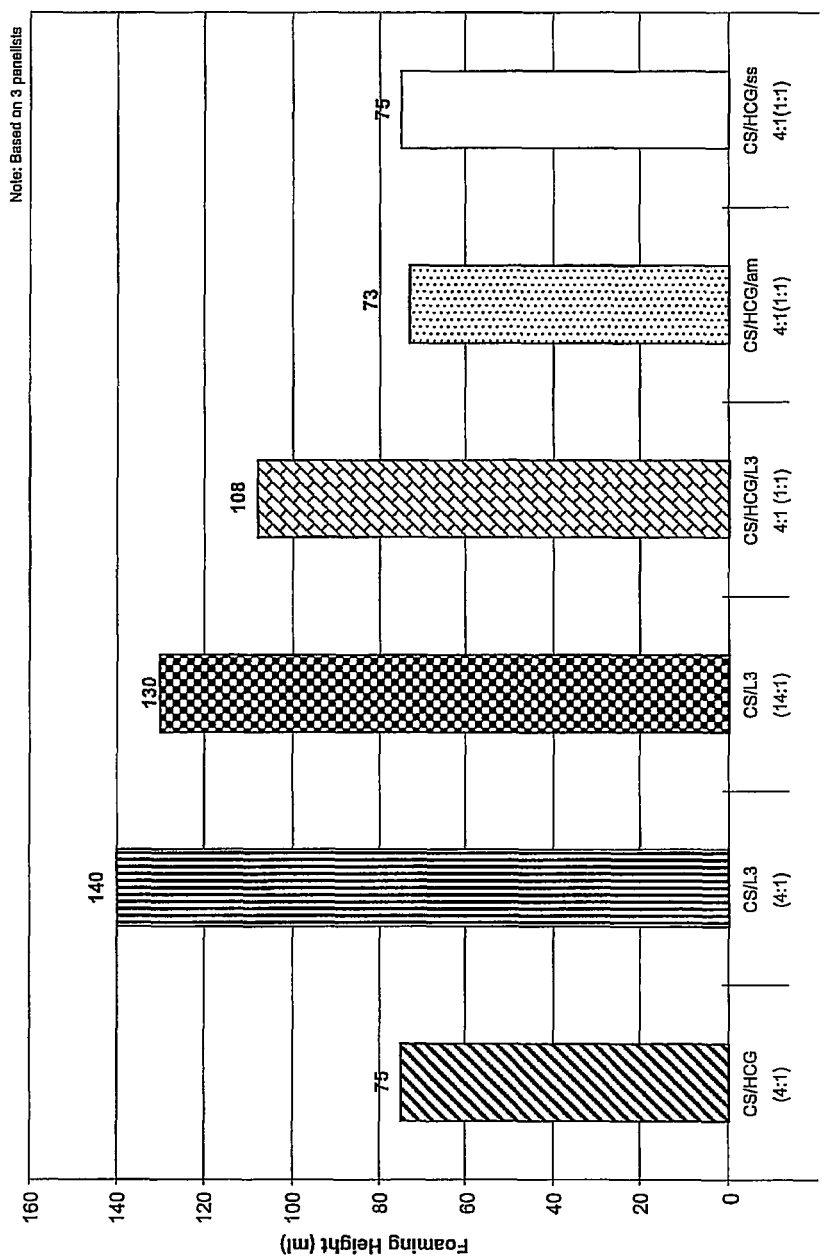

Hand foaming tests of the 6 compositions were conducted using the skin feel test method as described above. The comparative hand foaming results based on three panelists are shown in FIG. 19.

The results show that L3 of the presently described technology had better hand foaming performance than HCG, amphoacetate, or sulfosuccinate, when used alone or in combination with HCG.

Example 20

Comparative Hand Foaming Studies of Body Wash Compositions Containing HCG, L3 and/or Amphoacetate In this example, a series of four (4) compositions were prepared for hand wash foaming tests. The formulations of the 6 compositions were as follows:
1. CS-230/HCG (control): containing 12% by weight active SLES-2 (CS-230) and 3% by weight active CAPB (HCG) (4:1 ratio);
2. CS-230/L3: containing 12% by weight active CS-230 and 3% by weight active L3 (4:1 ratio);

3. CS-230/HCG/Amphoacetate: containing 12% by weight active CS-230 and 3% by weight active a secondary surfactant (4:1 ratio), wherein the secondary surfactant comprises HCG and sodium lauryl amphoacetate in a 1:1 ratio; and 4. CS-230/L3/Amphoacetate: containing 12% by weight active CS-230 and 3% by weight active a secondary surfactant (4:1 ratio), wherein the secondary surfactant comprises L3 and sodium lauryl amphoacetate in a 1:1 ratio.

Figure 20:
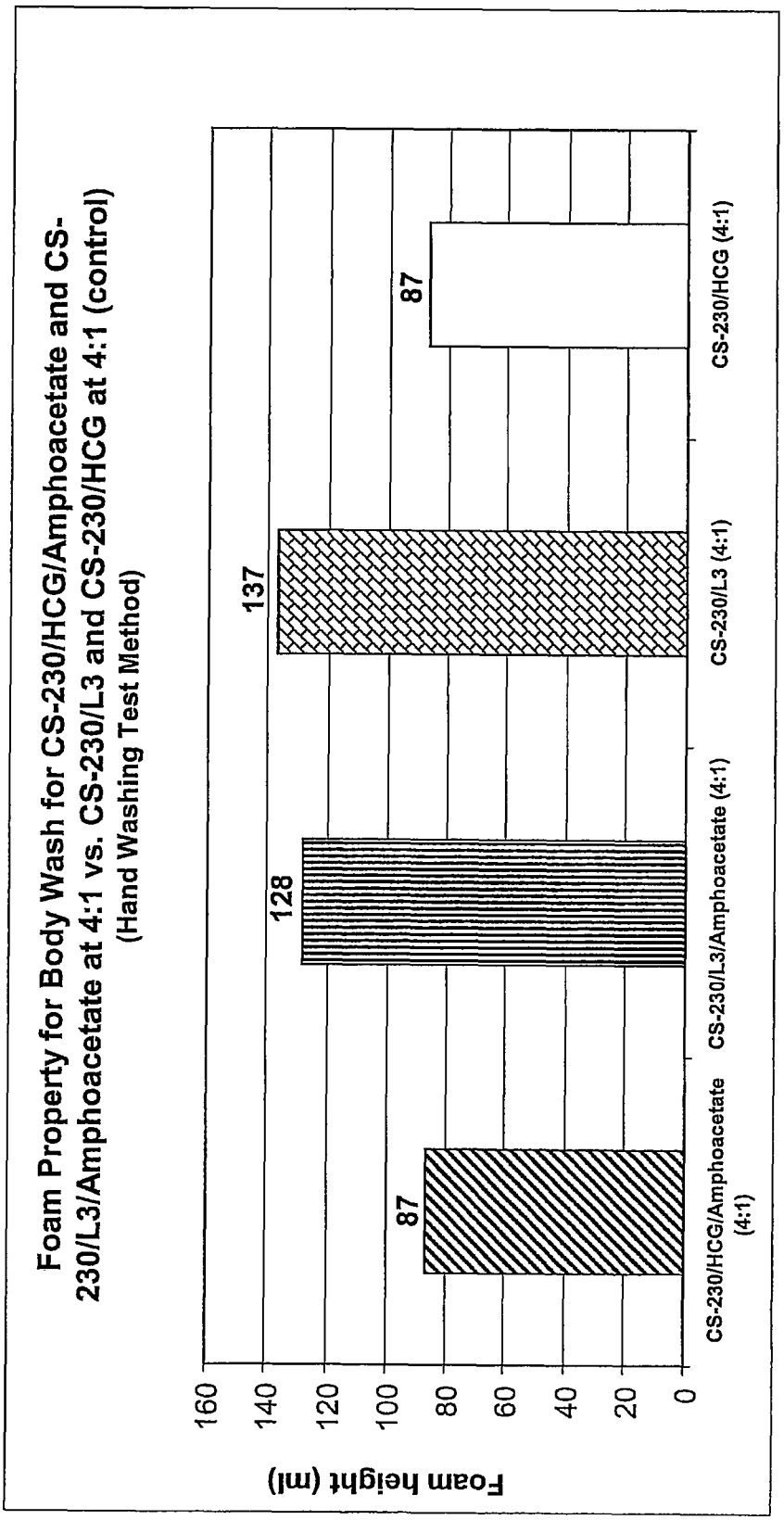

Hand foaming tests of the 4 compositions were conducted using the skin feel test method (also called hand washing test method) as described above. The comparative hand foaming results are shown in FIG. 20.

The results show that L3 of the presently described technology had substantially better hand foaming performance than HCG, when used alone. The results also show that when used in combination with amphoacetate in a 1:1 ratio, the L3 of the present technology still had substantially better hand foaming performance than HCG used in combination with amphoacetate in a 1:1 ratio.

Example 21

Preparation of Soap Bar Formulation Comprising LLL

Two syndet soap bars with the formulations shown in Table 3 were prepared using the following procedure: (1) weighing out all listed components, and amalgamating them in a one-gallon pail to form a mixture; (2) homogenizing the mixture in a 3-roll mill; (3) transferring the blend to a lab sigma plodder under a full control of the barrel temperature with cold water between about 30° C. to about 35° C. to remove heat generate from the extrusion pressure; (4) heating the head cone jacket to about 45° C. to facilitate the extrusion through the cone; and (5) cutting and stamping the extrudant into soap bars.

TABLE 3

Syndet Soap Bar Formulation

|  | SS-1 Weight % | SS-2 Weight % |
| --- | --- | --- |
| Sodium Cocoyl Isethionate | 50.00 | 50.00 |
| Stearic Acid | 26.00 | 26.00 |
| Sodium Tallow/Coco 80/20 Soap | 12.00 | 10.00 |
| Sodium Isethionate | 5.00 | 5.00 |
| Additives (Fragrance, $TiO_2$, and preservatives) | 1.5 | 1.5 |
| Lauryl Lactyllactate (L3) | 0.5 | 2.5 |
| Water | 5.00 | 5.00 |
| Total | 100.00 | 100.00 |

Two combo soap bars with the formulations shown in Table 4 were prepared using the following procedure: (1) roll-milling tallow/coco soap dry pellets; (2) blending in glycerine, fatty acids, L3, ALPHA-STEP® BSS-45 until uniform using a hydrofoil impeller at 300 ppm; (3) weighing out additive components; (4) amalgamating all components in a one-gallon pail to form a soap blend; (5) roll-milling the soap blend accompanied by testing moisture using Karl Fisher; (6) adjusting moisture to 12% if necessary while roll-milling; and (7) extruding and stamping the extrudant into soap bars.

TABLE 4

Combo Soap Bar Formulation

|  | CS-1 Weight % | CS-2 Weight % |
| --- | --- | --- |
| Sodium Tallow/Coconut 80/20 Soap pellets | 73.3 | 78.3 |
| Palm Stearine Fatty Acids | 6.0 | 0.0 |
| Stearic/Coconut Fatty Acid blend | 0.0 | 6.0 |
| Alpha Step ® BSS-45[a] | 4.0 | 0.0 |
| Lauryl Lactyllactate (L3) | 2.0 | 1.0 |
| Glycerine | 1.0 | 1.0 |
| NaCl | 0.3 | 0.3 |
| Additives (Fragrance, $TiO_2$ and preservatives) | 1.4 | 1.4 |
| Water | 12.00 | 12.0 |
| Total | 100.00 | 100.00 |

[a]This is an alpha sulfonated alkyl ester/sulfonated fatty acid SME/SFA blend.

The overall observation of the performance of the four soap bars is that Lauryl Lactyllactate, which is available from Stepan Company as STEPAN-MILD® L3, improved skin feel, foaming, and plasticity in both syndet and combo bars compared to commercial soap bars that contained betaine.

Example 22

Preparation of a Series of Wash Compositions with Different Amounts of Salicylic Acid A self-foaming wash with 0.5% salicylic acid, a regular wash with 1.0% salicylic acid, and a gel wash with 2.0% salicylic acid were prepared in this example according to the formulations shown in Table 5. The mixing procedure includes steps as set forth below.

In a suitable vessel equipped with heating and agitation capabilities, Deionized (D.I.) water, propylene glycol, and BIO-TERGE® AS-40 CG-P were charged. The charged materials were heated to 45-50° C. with mixing. STEPAN-MILD® L3 was added into the mixture with agitation. The mixture was kept at 45-50° C. with agitation until completely clear. Salicylic Acid was then added with agitation until completely clear and everything was dissolved, while maintaining the temperature at about 45° C. to about 50° C. The composition was cooled to room temperature with agitation. The pH of the composition was then adjusted to the desired value (about 5) with sodium hydroxide, and the viscosity was adjusted with sodium chloride.

TABLE 5

|  | Self-Foaming Wash Wt. % | Regular Wash Wt. % | Gel Wash Wt. % |
| --- | --- | --- | --- |
| D.I. Water | q.s. to 100.0 | q.s. to 100.0 | q.s. to 100.0 |
| Propylene Glycol | 2.00 | 2.00 | 2.00 |
| BIO-TERGE ® AS-40 CG-P (39.7% active sodium C14-16 olefin sulfonate) | 26.00 |  | 26.00 |
| STEOL ® CS-230 (25.85% active sodium laureth sulfate) |  | 58.03 |  |
| STEPAN-MILD ® L3 | 2.00 | 2.00 | 2.00 |
| Salicylic Acid | 0.50 | 1.00 | 2.00 |
| STEPAN ® PEG 6000 DS |  | 0.60 | 1.50 |
| Sodium Hydroxide | q.s. pH | q.s. pH | q.s. pH |
| Sodium Chloride | q.s. viscosity | 0.50 | 0.50 |
| pH | 4.3-4.6 | 4.3-4.6 | 4.3-4.6 |

TABLE 5-continued

|  | Self-Foaming Wash Wt. % | Regular Wash Wt. % | Gel Wash Wt. % |
|---|---|---|---|
| Viscosity @ 25° C., cps | Water thin | 7000 | 13,400 |
| Appearance | Light yellow, clear liquid | Light yellow, viscous clear liquid | Light yellow, viscous clear liquid |

Example 23

Preparation of an All Natural Body Wash and a Clear Body Wash

Two body washes with formulations as shown in Table 6 below are prepared in this example using procedures described herein. Into a suitable vessel equipped with mixing, heating and cooling capabilities, D.I. water, STEPANOL® WA-Extra, STEPAN-MILD® SLL-FB and STEPAN-MILD® L3 are added and mixed. The mixture is heated to about 130-135° F. When the reaction solution is clear, it is allowed to cool to room temperature. During the cooling process, flax extract is added at about 90° F., and mixed well. Preservatives, fragrance and dye are added, if desired, and mixed well. The viscosity can be adjusted with sodium chloride if desired, and the pH can be adjusted with sodium hydroxide or citric acid if necessary.

The two body wash compositions prepared are an all natural body wash and a clear body wash, respectively. By "all natural," it means that all ingredients in the composition are derived from natural materials.

TABLE 6

|  | All Natural Body Wash Wt. % Active | Clear Body Wash Wt. % Active |
|---|---|---|
| D.I. Water | q.s. to 100.0 | q.s. to 100.0 |
| STEPANOL® WA-Extra (Sodium Lauryl Sulfate) | 10.0 |  |
| STEPAN-MILD® SLL-FB (Sodium Lauroyl Lactylate) | 2.0 |  |
| STEOL® CS-230 (Sodium Laureth Sulfate) |  | 14.0 |
| STEPAN-MILD® L3 (Lauryl Lactyllactate) | 1.0 | 1.0 |
| Flax Extract 120 | 0.50 |  |
| SilPlex J-2S (Silicone Quaternium-20) |  | 1.0 |
| Glycerin |  | 0.8 |
| Preservative, dye, fragrance | q.s. | q.s. |
| Sodium Chloride | q.s. | q.s. |
| Sodium Hydroxide | q.s. | q.s. |
| Citric Acid | q.s. | q.s. |

Example 24

Preparation of a Skin Lotion

A skin lotion with a formulation shown in Table 7 below is prepared in this example using a procedure similar to the one described below.
Prepare water phase: D.I. Water and BRIJ® 78 are charged into a vessel, and mixed well to form a water phase mixture. The water phase mixture is heated to about 170-175° F. Prepare Oil phase: In a separate container, STEPAN-MILD® L3, IPP, cetyl alcohol and GMS are added and mixed to form an oil phase mixture. The oil phase mixture is heated to about 170-175° F. With increased agitation of the water phase, the oil phase is slowly added into the water phase. The resulting mixture is allowed to emulsify for approximately 20-25 minutes, and then is allowed to cool to about 80° F. Any preservative, color, or dye can be slowly added, if desired. The pH of the resulting composition can be adjusted with citric acid or sodium hydroxide to a desired value.

TABLE 7

|  | Wt. % Active |
|---|---|
| D.I. Water | q.s. to 100.0 |
| BRIJ® 78 Steareth-20 (Unichema) | 1.0 |
| STEPAN-MILD® L3 (Lauryl Lactyllactate) | 3.0 |
| IPP | 10.0 |
| Cetyl Alcohol | 3.0 |
| STEPAN® GMS PURE (Glycerol Monostearate) | 2.0 |
| Preservative, dye, fragrance | q.s. |
| Sodium Hydroxide | q.s. |
| Citric Acid | q.s. |

Example 25

Preparation of a Solid Antiperspirant

A solid antiperspirant with a formulation shown in Table 8 below is prepared in this example using the following procedure: The ingredients 245 Fluid, Lanette 18 Deo, Ozokerite Wax, and Castor Oil Wax MP-80 are combined in a suitable vessel, mixed and heated to about 70° C. When all of the ingredients are melted, Talc and Reach AZP are added and mixed well for approximately 20 minutes. The mixture is then cooled to about 45° C., then poured into containers and allowed to cool to ambient temperature.

TABLE 8

| Ingredients | Wt. % Active |
|---|---|
| Dow Corning 245 Fluid (Dow Corning) Cyclopentasiloxane | 40.5 |
| STEPAN-MILD® L3 (Lauryl Lactyllactate) | 10.0 |
| Lanette 18 Deo (Henkel) Stearyl Alcohol | 15.0 |
| Ozokerite Wax (Strahl & Pitsch Inc.) Ozokerite Wax | 5.0 |
| Castor Wax MP-80 (CasChem) Hydrogenated Castor Oil | 1.5 |
| Talc, USP, Bacteria Controlled 1745 (Whittaker, Clark & Daniels) | 8.0 |
| Reach AZP 701 (Reheis) Aluminum Zirconium Tetrachlorohydrex GLY | 20.0 |

Example 26

Foaming and Detergency Performance Tests for Detergent Compositions Using Alkyl Lactyllactates as Secondary Surfactants The foaming performance of L3 as a component in detergent formulations is expected to show that the incorporation of L3 results in foaming performance that is comparable or better than in control formulations. One formulation for a heavy duty detergent incorporating L3 is shown in Table 9 below.

TABLE 9

| Ingredient | Actives (wt. %) |
|---|---|
| D.I. Water | 71.74 |
| NABIOSOFT ® S-101(31.6% active dodecylbenzene sulfonate) | 5.60 |
| L3 | 1.00 |
| STEPANATE ® SXS (41% active Sodium Xylene Sulfonate | 0.93 |
| TEA 99% | 0.93 |
| NEODOL ® 25-7 | 16.80 |
| Oleic Acid | 2.00 |
| Sodium Carbonate | 1.00 |
| Total | 100.00 |

Based upon the results and the attributes of the alkyl lactyllactate compositions of the present technology, it is believed that L3 can be incorporated into detergent formulations, such as, for example, heavy duty detergents, as a secondary surfactant in lieu of, or in addition to, anionic surfactants. It is also believed that incorporating L3 with different anionic surfactants in detergent formulations will result in synergistic improvements in cleaning performance.

Example 27

Performance Tests for Detergent Compositions Using Alkyl Lactyllactates as Secondary Surfactants A series of five light duty liquid dish detergent formulations were prepared, each of which contained 17.51% by weight active sodium alkylbenzene sulfonate, 8.17% by weight active methyl ester sulfonate, 4.32% by weight active alkyl ether sulfate, and 3% by weight active of a secondary surfactant (10:1 ratio). The secondary surfactants were (1) NINOL® 40-CO (Control), (2) AMMONYX® LMDO (Control), (3) STEPAN-MILD® L3, (4) a blend of NINOL® 40-CO and STEPAN-MILD® L3, and (5) a blend of AMMONYX® LMDO and STEPAN-MILD® L3.

All of the formulations were clear at room temperature. The viscosity results of each formulation are shown in Table 10 below.

TABLE 10

| Sample Number | Secondary Surfactant | Viscosity in Formulation |
|---|---|---|
| 1 | NINOL ® 40-CO | 590 cps |
| 2 | AMMONYX ® LMDO | 1,225 cps |
| 3 | STEPAN-MILD ® L3 | 570 cps |
| 4 | NINOL ® 40-CO & STEPAN-MILD ® L3 | 650 cps |
| 5 | AMMONYX ® LMDO & STEPAN-MILD L3 | 850 cps |

The mixer foam test results are shown in Table 11 below.

TABLE 11

| Sample | Test | Soil (g) | Average |
|---|---|---|---|
| 1 (NINOL ® 40-CO) | 1 | 1.63 | 1.73 |
|  | 2 | 1.82 |  |
| 2 (AMMONYX ® LMDO) | 1 | 1.88 | 1.98 |
|  | 2 | 2.08 |  |
| 3 (STEPAN-MILD ® L3) | 1 | 1.65 | 1.66 |
|  | 2 | 1.67 |  |
| 4 (40-CO & L3) | 1 | 1.67 | 1.72 |
|  | 2 | 1.77 |  |
| 5 (LMDO & L3) | 1 | 1.63 | 1.67 |
|  | 2 | 1.71 |  |

The experimental error of the mixer foam test is estimated to be +/−0.2 g. The samples containing STEPAN-MILD® L3 performed as well as the control formulations.

The Baumgartner test results are shown in Table 12 below.

TABLE 12

| Sample | Slide # | Grams Soil Removed | % Soil Removed | Average |
|---|---|---|---|---|
| 1 (NINOL ® 40-CO) | 1 | 0.1084 | 44.41% | 41.88% |
|  | 2 | 0.1082 | 41.06% |  |
|  | 3 | 0.0985 | 40.15% |  |
| 2 (AMMONYX ® LMDO) | 1 | 0.1044 | 41.15% | 40.22% |
|  | 2 | 0.0987 | 40.27% |  |
|  | 3 | 0.1008 | 39.24% |  |
| 3 (STEPAN-MILD ® L3) | 1 | 0.0584 | 23.05% | 23.06% |
|  | 2 | 0.0602 | 23.30% |  |
|  | 3 | 0.0595 | 22.83% |  |
| 4 (L3 & 40-CO) | 1 | 0.0764 | 29.79% | 30.25% |
|  | 2 | 0.0804 | 31.35% |  |
|  | 3 | 0.0782 | 29.61% |  |
| 5 (L3 & LMDO) | 1 | 0.0796 | 31.80% | 30.96% |
|  | 2 | 0.0771 | 29.27% |  |
|  | 3 | 0.0788 | 31.80% |  |

The experimental error for the Baumgartner test is approximately +/−5.0% grease removal. Although the results of all of the samples containing STEPAN-MILD® L3 were lower than those of the LMDO and 40-CO controls, the test result of the sample containing the L3 and LMDO blend was within experimental error as compared to those of the controls.

The Mini-Plate test results are shown in Table 13 below.

TABLE 13

| Sample | Test | Mini-Plates | Average |
|---|---|---|---|
| 1 (NINOL ® 40-CO) | 1 | 9 | 8.5 |
|  | 2 | 8 |  |
| 2 (AMMONYX ® LMDO) | 1 | 12 | 10.0 |
|  | 2 | 9 |  |
|  | 3 | 9 |  |
| 3 (STEPAN-MILD ® L3) | 1 | 9 | 9.0 |
|  | 2 | 9 |  |
| 4 (40-CO & L3) | 1 | 9 | 9.0 |
|  | 2 | 9 |  |
| 5 (LMDO & L3) | 1 | 10 | 10.0 |
|  | 2 | 10 |  |

The experimental error of the Mini-Plate test is +/−1 mini-plate. For purposes of comparison, it should be noted that this type of test is sometimes reported in "plates" instead of "mini-plates", and that one mini-plate equals three plates. In this testing, the samples containing STEPAN-MILD® L3 performed as well as the controls.

The Shake Foam Test results are shown in Table 14 below.

TABLE 14

| Sample | Sample # | Without Soil | | | With Soil | | |
|---|---|---|---|---|---|---|---|
|  |  | 1 | 2 | Average | Initial | 5 Minute | Average |
| 1 | Initial | 310 | 320 | 315 | 265 | 265 | 265 |
|  | 5 Minute | 310 | 320 | 315 | 260 | 260 | 260 |

TABLE 14-continued

| | | Without Soil | | | With Soil | | |
|---|---|---|---|---|---|---|---|
| Sample | Sample # | 1 | 2 | Average | Initial | 5 Minute | Average |
| 2 | Initial | 450 | 480 | 465 | 300 | 300 | 300 |
| | 5 Minute | 450 | 480 | 465 | 300 | 300 | 300 |
| 3 | Initial | 420 | 415 | 417.5 | 300 | 290 | 295 |
| | 5 Minute | 420 | 410 | 415 | 300 | 290 | 295 |
| 4 | Initial | 390 | 380 | 385 | 275 | 250 | 262.5 |
| | 5 Minute | 380 | 370 | 375 | 275 | 250 | 262.5 |
| 5 | Initial | >500 | >500 | >500 | 285 | 280 | 282.5 |
| | 5 Minute | >500 | >500 | >500 | 285 | 280 | 282.5 |

The experimental error of this test is approximately +/−20 ml. All of the results "With Soil" were equal. It should be noted that the 50:50 blend of L3:LMDO exhibited some synergy based on the extremely high shake foam results with no soil.

Example 28

Preparation of Roll-On Anti-Perspirant

A roll-on antiperspirant formulation shown in Table 15 is prepared using a procedure described as follows: Deionized Water and Aluminum Chloride are combined and heated to about 150° F.-155° F. with moderate agitation. At about 150° F. to about 155° F., BRIJ 72, BRIJ 78, and STEPAN-MILD® L3 are added with increased agitation. "Chiral L3/Meso L3/mixture of L2/L3" in Table 15 and other tables means that the L3 used can be a chiral L3 made from L-lactide or D-lactide, a racemic L-3 made from meso-lactide, a mixture of L2 and L3 made from a lactic acid process, for example, or a mixture thereof.

The mixture of the ingredients is continually heated to about 160° F. to about 165° F., and held within the temperature range for approximately 15 minutes. The mixture is then cooled to room temperature. At room temperature, preservatives and fragrance are added. The pH of the product can be adjusted with citric acid or sodium hydroxide to 3.5-4.0, if necessary.

TABLE 15

| Ingredients | Wt. % Active |
|---|---|
| Aluminum Chlorohydrate, 50% solution | 40.0 |
| BRIJ 78 (Uniqema) Steareth-20 | 0.6 |
| BRIJ 72 (Steareth-2) | 1.8 |
| STEPAN-MILD ® L3 (Chiral L3/Meso L3/mixture of L2/L3) | 3.0 |
| Preservative, Fragrance | q.s. |
| Citric Acid, 50% solution | q.s. |
| Sodium Hydroxide, 50% solution | q.s. |

Example 29

Preparation of UA/UVB Protective Lotion

A protective lotion with a formulation shown in Table 16 is prepared using a procedure described as follows: A water phase is prepared by charging a vessel with deionized water and BRIJ 78. The mixture is mixed and heated to about 170° F.-175° F. An oil phase is prepared in a separate container by combining STEPAN-MILD® L3, cetyl alcohol, and HALLSTAR® GMS PURE. Sunscreen agent (PARSOL MCX, ESCALOL 587, PARSOL 1789, ESCALOL 567) is added to the oil phase, which is then heated to about 170° F.-175° F. Agitation of the water phase is increased, and the oil phase is slowly added into the water phase. The mixture is emulsified for approximately 20-25 minutes, and allowed to cool to about 80° F. Preservative, dye, and fragrance are added, if desired. The pH is adjusted with citric acid or sodium hydroxide to about 5.5-6.5.

TABLE 16

| Ingredients | Wt. % Active |
|---|---|
| Deionized Water | q.s. to 100.0 |
| BRIJ 78 (Uniqema) Steareth-20 | 1.0 |
| STEPAN-MILD ® L3 (Chiral L3/Meso L3/mixture of L2/L3) | 10.0 |
| Lipocol C (Lipo) Cetyl Alcohol | 3.0 |
| HALLSTAR ® GMS PURE | 2.0 |
| PARSOL MCX (Givaudan-Roure) Ethylhexyl-p-Methoxycinnamate | 7.5 |
| ESCALOL 587 (ISP) Octyl Salicylate | 5.0 |
| PARSOL 1789 (Roche) Avobenzone | 2.0 |
| ESCALOL 567 (ISP) Benzophenone-3 | 3.0 |
| Preservative, Dye, Fragrance | q.s |
| Citric Acid | q.s. |
| Sodium Hydroxide | q.s. |

Example 30

Preparation of Sunscreen W/O Lotion with Titanium Dioxide

A sunscreen with a formulation shown in Table 17 below is prepared using a procedure described as follows: A water phase is prepared by mixing deionized water and STEPAN-QUAT™ ML. An oil phase is prepared by combining Silicone DC-345, STEPAN-MILD® L3, ABIL EM-90, MT-100T, and SALCARE SC-95. The water phase is then added into the oil phase, and mixed well for approximately 15-20 minutes. Preservative, dye, and fragrance are then added, and mixed in a homogenizer for approximately 3-5 minutes at 5000 rpm.

TABLE 17

| Ingredients | Wt. % Active |
|---|---|
| Deionized Water | q.s. to 100 |
| STEPANQUAT ™ ML | 2.0 |
| Silicone DC-345 (Dow Coming) Cyclomethicone | 10.0 |
| STEPAN-MILD ® L3 (Chiral L3/Meso L3/mixture of L2/L3) | 10.0 |
| ABIL EM-90 (Goldschmidt) Cetyl Dimethicone Copolyol | 1.0 |
| MT-100T (Tri-K) Titanium Dioxide and Aluminum Hydroxide and Stearic Acid | 8.0 |
| SALCARE SC-95 (Ciba) Polyquaternium-37 + Mineral Oil + PPG-1 Trideceth-6 | 2.0 |
| Preservative, Dye, Fragrance | q.s. |

Example 31

Preparation of Sunless Tanning Lotion

A tanning lotion with a formulation shown in Table 18 is prepared using a procedure described as follows. A water phase is prepared by mixing deionized water and glycerin. The water phase is heated to about 160° F. An oil phase is prepared by mixing BRIJ 78, STEPAN-MILD® L3, HALLSTAR® GMS PURE, Lipocol C (Lipo) cetyl alcohol, and WECOBEE® S. The oil phase is heated to about 165° F., which is then added to the water phase with increased agitation at about 165° F. for approximately 20-25 minutes. The mixture is allowed to cool to room temperature. During the cooling, glydant is added at 120° F. Dihydroxyacetone, which is premixed with water, is added at 95° F. The mixture is mixed well, then its pH is adjusted to about 5.5-6.0.

TABLE 18

| Ingredients | % Active |
|---|---|
| Deionized Water | q.s. to 100 |
| Glycerin | 3.5 |
| BRIJ 78 (Uniqema) Steareth-20 | 0.4 |
| STEPAN-MILD ® L3 (Chiral L3/Meso L3/mixture of L2/L3) | 10.0 |
| HALLSTAR ® GMS PURE | 3.0 |
| Lipocol C (Lipo) Cetyl Alcohol | 2.0 |
| WECOBEE ® S (Hydrogenated Vegetable Oil) | 2.5 |
| DOW CORNING 200 Fluid, 350 cps (Dow Corning) Dimethicone | 1.0 |
| Glydant (Lonza) DMDM Hydantoin | 0.25 |
| Dihydroxyacetone (EMD) | 3.5 |

Example 32

Preparation of Skin Lotion with Antioxidants

A skin lotion with a formulation shown in Table 19 is prepared using a procedure described as follows: A water phase is prepared by mixing deionized water and BRIJ 78 in a vessel, which is heated to about 170° F.-175° F. An oil phase is prepared in a separate container by combining STEPAN-MILD® L3, cetyl alcohol, and HALLSTAR® GMS PURE. The oil phase is heated to about 170° F.-175° F. With increased agitation of the water phase, the oil phase is slowly added into the water phase. The mixture is emulsified for approximately 20-25 minutes, and allowed to cool to 80° F. Vitamin A palmitate and Vitamin E Acetate are then added. Preservative, color, and dye can be added, if desired. The pH of the mixture can be adjusted with citric acid or sodium hydroxide to about pH 5.5-6.5.

TABLE 19

| Ingredients | % Active |
|---|---|
| Deionized Water | q.s. to 100 |
| BRIJ 78 (Uniqema) Steareth-20 | 1.0 |
| STEPAN-MILD ® L3 (Chiral L3/Meso L3/mixture of L2/L3) | 10.0 |
| Lipocol C (Lipo) Cetyl Alcohol | 3.0 |
| HALLSTAR ® GMS PURE | 2.0 |
| Vitamin A Palmitate | 0.1-25 |
| Vitamin E Acetate | 0.1-25 |
| Preservative, Color, Dye | q.s. |
| Citric Acid | q.s. |
| Sodium Hydroxide | q.s. |

Example 33

Preparation of Hair Conditioner

A hair conditioner with a formulation shown in Table 20 below is prepared using a procedure described as follows: Deionized water and Lexamine S-13 are added into a suitable vessel equipped with heating, cooling, and mixing capabilities. The mixture was heated to about 155° F.-160° F. (62° C.-72° C.). AMMONYX® 4, AMMONYX® CETAC, and cetyl alcohol are added into the mixture. The mixture is emulsified for about 30 minutes, and allowed to cool to about 120° F. to about 125° F. (48° C.-52° C.). Potassium chloride dissolved in water is added into the mixture followed by the addition of STEPAN-MILD® L3. The pH of the mixture is adjusted to about 3.5-4.5 with citric acid or sodium hydroxide, if necessary. Preservative, color, and fragrance are added, if desired, and the mixture is cooled to room temperature.

TABLE 20

| Ingredients | % Active |
|---|---|
| Deionized Water | q.s. to 100 |
| Lexamine S-13 (Stearamidopropyl Dimethylamine) | 0.15 |
| AMMONYX ® 4 (Stearalkonium Chloride) | 5.55 |
| AMMONYX ® CETAC (Cetrimonium Chloride) | 3.85 |
| Lipocol C (Lipo) Cetyl Alcohol | 3.0 |
| Potassium Chloride | 0.3 |
| STEPAN-MILD ® L3 (Chiral L3/Meso L3/mixture of L2/L3) | 2.0 |
| Citric Acid, 50% solution | q.s. |
| Sodium Hydroxide, 50% solution | q.s. |
| Fragrance, Dye, Preservative | q.s. |

Example 34

Preparation of Shampoo

A shampoo with a formulation shown in Table 21 is prepared using a procedure described as follows: Polyquaternium-10 is incorporated into deionized water, followed by the addition of STEPANOL® AM, STEPANOL® WA, HALLSTAR® EGAS, and STEPAN-MILD® L3. The mixture is heated to about 160° F. to about 165° F., and held at this temperature for approximately 20-25 minutes. The mixture is then allowed to cool to room temperature. During the cooling, glycerin and SILPLEX J-2S are added at 100° F., and mixed well. Preservative, fragrance, and dye are added at room temperature. The pH of the mixture is adjusted with citric acid or sodium hydroxide to about pH 5.5-6.5, and the viscosity of the mixture is adjusted with ammonium chloride to a desired viscosity in the range of from about 5,000 to about 11,000 cps, more preferably, from about 8,000 to about 10,000 cps.

TABLE 21

| Ingredients | % Active |
|---|---|
| Deionized Water | q.s. to 100 |
| UCare JB-400 Amerchol (Polyquaternium-10) | 0.15 |
| STEPANOL ® AM (Ammonium Lauryl Sulfate) | 7.0 |
| STEPANOL ® WA (Sodium Lauryl Sulfate) | 6.0 |
| STEPAN-MILD ® L3 (Chiral L3/Meso L3/mixture of L2/L3) | 2.0 |
| HALLSTAR ® EGAS (Glycol Stearate/Stearamide AMP) | 0.5 |
| Glycerin | 0.5 |
| SILPLEX J-2S (Silicone Quaternium) | 0.5 |
| Fragrance, Dye, Preservative | q.s. |
| Citric Acid, 50% solution | q.s. |
| Sodium Hydroxide, 50% solution | q.s. |
| Ammonium Chloride | q.s. |

Example 35

Preparation of a Lauryl Lactyllactate Product from Lactic Acid

About 169 g (1.6 mol) lactic acid, 47 mL (0.2 mol) C12-14 fatty alcohol, and 5 g (2.4% on total mass) pTSA were placed into a 500 mL four-neck flask equipped with overhead mechanical stirrer, $N_2$ inlet and outlet, thermocouple/temp controller/heating mantel, and condenser fitted with a Dean-Stark trap. The reaction mixture was stirred and heated to 185° C. After stirring at this temperature for approximately 4 hours, over which time 50 mL of water was collected, the reaction was allowed to cool and a sample was taken for reaction completion. The mixture was cooled and washed with brine (3×80 mL) and neutralized with saturated NaHCO$_3$ (aq). The mixture was dried over Na$_2$SO4 and filtered.

GC analysis shows that the reaction product contains lauryl lactyllactate (L3) and lauryl lactate (L2) in a ratio of about 1:0.7.

Example 36

Study of Surface Properties of Surfactant Blends Containing Lauryl Lactyllactate The effect of lauryl lactyllactate (L3) to reduce the critical micelle concentration (CMC) and surface area per molecule of seven commonly used surfactants were tested in this example. The L3 tested was available from Stepan Company under the trade name STEPAN-MILD® L3. The seven surfactants tested are shown in Table 22 below:

TABLE 22

| | |
|---|---|
| STEOL ® CS-230 | Sodium salt of C$_{12}$-C$_{14}$ alkyl ethoxy sulfate with 2 moles ethylene oxide per mole of alcohol |
| STEPANOL ® WA-EXTRA | Sodium salt of C$_{12}$-C$_{14}$ alkyl sulfate |
| ALPHA-STEP ® PC-48 | average 6:1 ratio of sodium sulfonted methyl C$_{12}$-C$_{18}$ ester (and) disodium sulfonated C$_{12}$-C$_{18}$ fatty acid |
| BIOTERGE ® PAS-8S | Sodium octane sulfonate |
| AMPHOSOL ® HCG | Cocamidopropyl betaine |
| BIOSOFT ® N91-8 | Alcohol ethoxylates based on a C9-11 synthetic alcohol |
| AMMONYX ® CETAC | Cetrimonium Chloride |

Seven control surfactant compositions (Controls 1-7) containing one or two of the seven conventional surfactants only, and nine sample surfactant compositions (Samples 1A-C and 2-7) containing one or two of the conventional surfactants and L3 of the present technology, were prepared in accordance with the formulations shown in Tables 23A & 23B. The CMC of each surfactant composition was measured with Krüss K12 tensiometer (Kruss USA, Matthews, N.C., USA) via automatic titration. The temperature was controlled at 25° C. Surface area per molecule was calculated according to Gibbs equation. The test results are shown in Tables 23A and 23B.

TABLE 23A

Surface Properties of Surfactant Blends Containing Lauryl Lactyllactate

| | Control 1 Act. % | Sample 1A Act. % | Sample 1B Act. % | Sample 1C Act. % | Control 2 Act. % | Sample 2 Act. % | Control 3 Act. % | Sample 3 Act. % |
|---|---|---|---|---|---|---|---|---|
| STEOL CS-230 | 15 | 14 | 12 | 10.91 | | | | |
| STEPANOL WA-EXTRA | | | | | 15 | 14.7 | | |
| ALPHA-STEP PC-48 | | | | | | | 12 | 10.91 |
| AMPHOSOL HCG | | | | 2.73 | | | 3 | 2.73 |
| STEPAN-MILD L3 | | 1 | 3 | 1.36 | | 0.3 | | 1.36 |
| Water | q.s. to 100 | q.s. to 100 | q.s. to 100 | q.s. to 100 | q.s. to 100 | q.s. to 100 | q.s. to 100 | q.s. to 100 |
| Appearance | Clear liquid | Clear liquid | Clear liquid | Clear liquid | Clear liquid | Clear liquid | Clear liquid | Clear liquid |
| CMC (mg/L) | 171.1 | 25.8 | 10 | 16.9 | 184.9 | 47.15 | 35.1 | 16 |
| Surface Area per Molecule (Å$^2$) | 49.9 | 28 | 27.1 | 26.3 | 38.3 | 24.1 | 30.1 | 26.4 |

TABLE 23B

Surface Properties of Surfactant Blends Containing Lauryl Lactyllactate

| | Control 4 Act. % | Sample 4 Act. % | Control 5 Act. % | Sample 5 Act. % | Control 6 Act. % | Sample 6 Act. % | Control 7 Act. % | Sample 7 Act. % |
|---|---|---|---|---|---|---|---|---|
| BIOTERGE PAS-8S | 15 | 14 | | | | | | |
| AMPHOSOL HCG | | | 15 | 12 | | | | |
| BIOSOFT N91-8 | | | | | 15 | 14 | | |
| AMMONYX CETAC | | | | | | | 15 | 14 |
| STEPAN-MILD L3 | | 1 | | 3 | | 1 | | 1 |
| Water | q.s. to 100 | q.s. to 100 | q.s. to 100 | q.s. to 100 | q.s. to 100 | q.s. to 100 | q.s. to 100 | q.s. to 100 |
| Appearance | Clear liquid | Clear liquid | Clear liquid | Clear liquid | Clear liquid | Clear liquid | Clear liquid | Clear liquid |
| CMC (mg/L) | 10680 | 33.57 | 15.3 | 6.6 | 346 | 16.6 | 292 | 11.1 |
| Surface Area per Molecule (Å$^2$) | 41.5 | 28 | 28.1 | 23.59 | 56.1 | 38.5 | 56.3 | 21.9 |

It was surprisingly found that for each conventional surfactant tested, the surfactant blend comprising lauryl lactyllactate had significantly lower critical micelle concentration (CMC) than the one that did not contain lauryl lactyllactate. It was also unexpectedly found that lauryl lactyllactate effectively reduced the area/molecule in the surfactant blend comprising lauryl lactyllactate. The reduced area/molecule indicated improved molecular packing of surfactant at the air/water interface. The unexpected results demonstrated synergistic properties of surfactant blends comprising lauryl lactate.

The efficiency of lauryl lactyllactate in CMC reduction was particularly surprising. As shown in by Control 4 and Sample 4, the CMC reduction in a blend of L3 and PAS-8S was more than 99% compared to the composition containing only PAS-8S. It was also found that lauryl lactyllactate was compatible with different kinds of surfactants, including, for example, anionic, nonionic, cationic and amphoteric. Lauryl lactyllactate has shown the capability of reducing CMC and area/molecule in all these surfactant categories. Samples 1A-C and 2-4 demonstrated anionic surfactant blends. Samples 5-7 demonstrated amphoteric, nonionic and cationic surfactant blends, respectively. The CMC reduction in these examples was from about 30% to about 99%. The reduction in area/molecule was from about 10% to about 60%.

Example 37

Study of Rheological Properties of Fabric Softeners Containing Lauryl Lactyllactate The ability of lauryl lactyllactate to be used as a rheological modifier was studied in this experiment. The control composition contained only methyl bis[ethyl (tallowate)]-2-hydroxyethyl ammonium methyl sulfate, which is commercially available from Stepan Company as STEPANTEX® VT-90. The two samples of the present technology contains a blend of STEPANTEX® VT-90 and lauryl lactyllactate in the ratios of 4:1 and 3:2, respectively. The viscosities of the three compositions at 20° C., 30° C., and 40° C. were tested, and the results are shown in Table 24 below.

TABLE 24

Rheological Properties of Fabric Softeners Containing Lauryl Lactyllactate

| | Control Weight % | Sample 1 Weight % | Sample 2 Weight % |
|---|---|---|---|
| STEPANTEX VT-90 (Gross Weight) | 100 | 80 | 60 |
| STEPANTEX VT-90 (Active %) | 90 | 72 | 54 |
| Lauryl lactyllactate | | 20 | 40 |
| Total Solids % | 90 | 92 | 94 |
| Viscosity at 20° C. (cps) | 43820 | 9712 | 7337 |
| Viscosity at 30° C. (cps) | 10742 | 1021 | 558 |
| Viscosity at 40° C. (cps) | 1336 | 440 | 135 |

The results shown in Table 24 demonstrated the viscosity reduction property of lauryl lactyllactate in fabric softeners. By incorporating lauryl lactyllactate in a fabric softener, the viscosity of the surfactant system was significantly reduced.

Example 38

Comparative Viscosity Salt Response and Foaming Studies of Lauryl Lactyllactates of Different Chirality Three compositions were prepared, each of which contained 12% by weight active SLES-2 (CS-230) and 3% by weight active of L-lauryl lactyllactate made from L-lactide ("L3 using L-lactide"), lauryl lactyllactate made from a mixture of L-lactide (15%) and meso-lactide (85%) ("L3 using L/Meso lactide"), or racemic lauryl lactyllactate made from racemic lactide ("L3 using racemic lactide"). No oil was added to the compositions.

Figure 21:
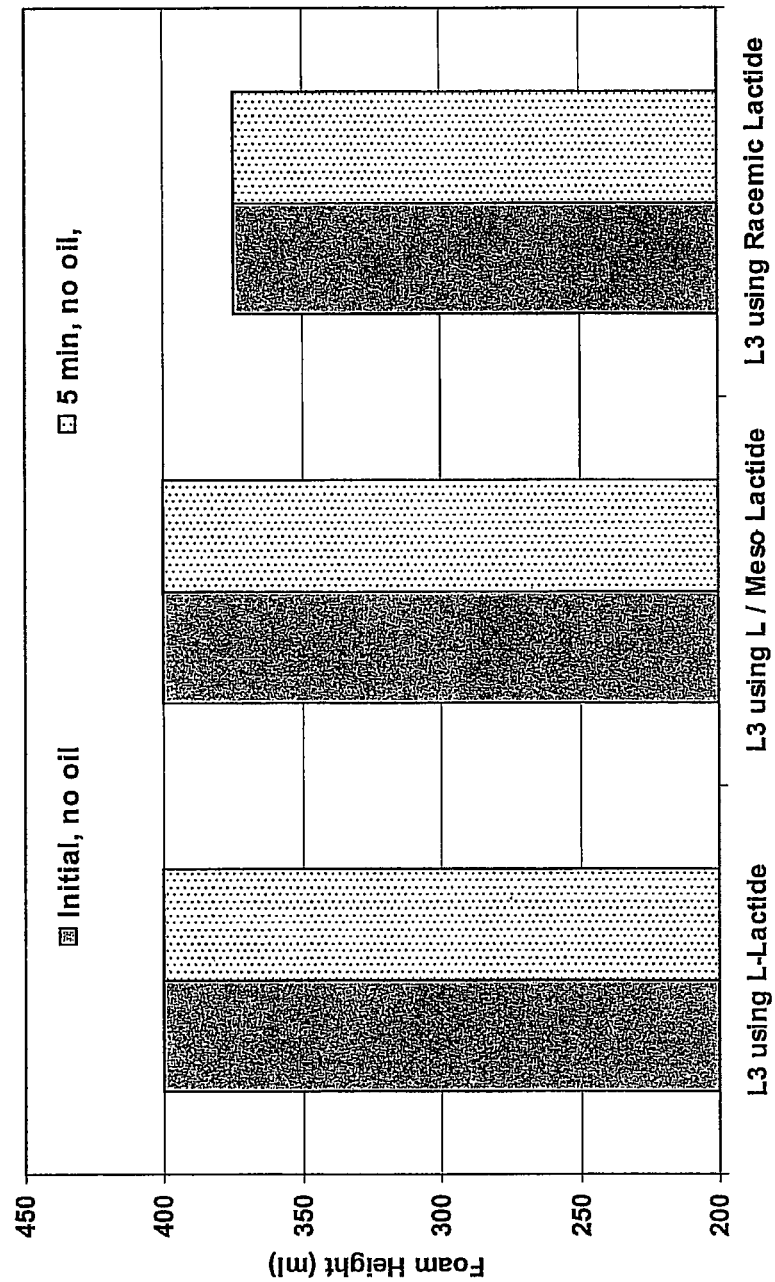
FIG. 21 shows the foam performance test (with no oil) results of three compositions comprising lauryl lactyllactate made from (1) L-lactide or (2) a 15:85 mixture of L-lactide and meso-lactide or (3) racemic lactide.

Foaming performance of each composition was tested by the shake foam test method (also called cylinder inversion test method) as described above. The foaming results of the three compositions with no oil (both initial and after five minutes) were recorded and shown in FIG. 21.

The results with no oil show that the experimental compositions comprising L3 using L-lactide or L3 using L/Meso-lactide are comparable, and both have higher foam heights than the composition comprising L3 using racemic lactide.

Figure 22:
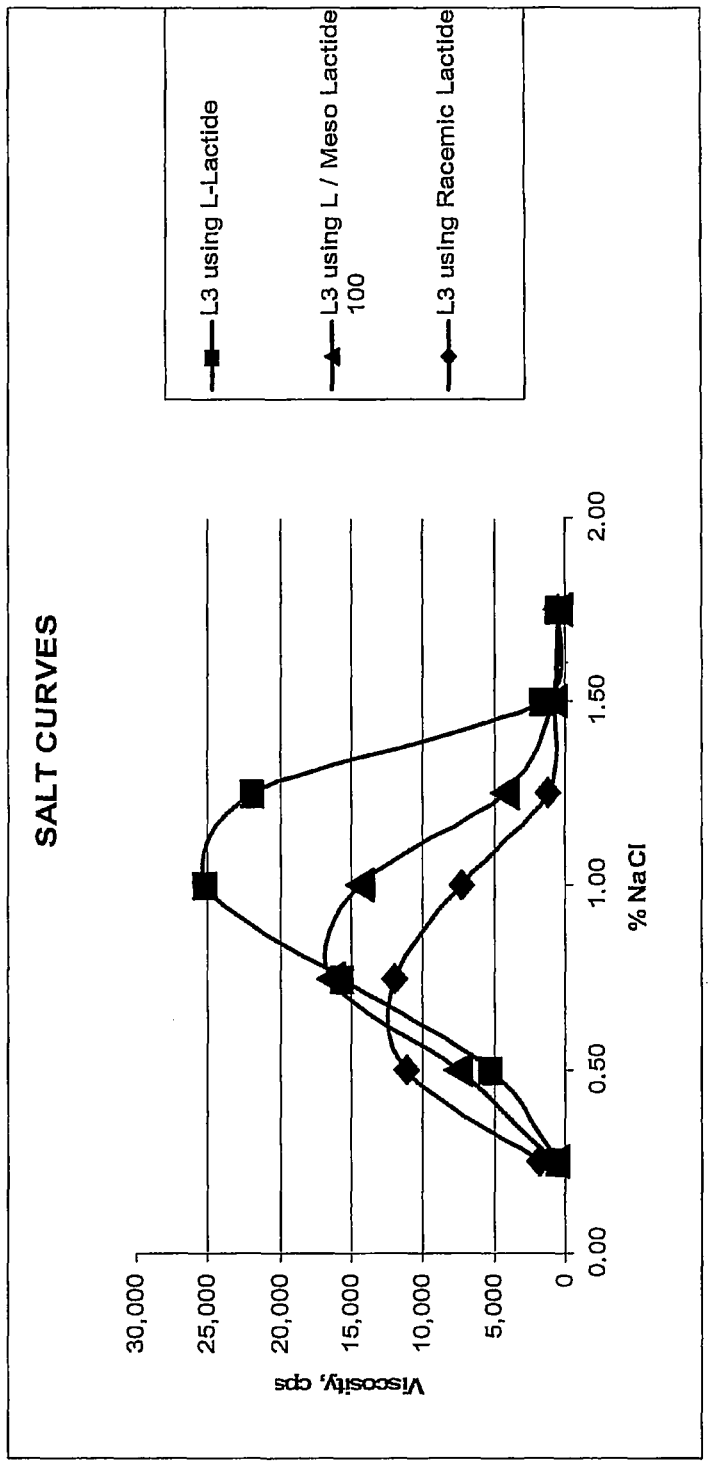
FIG. 22 shows the viscosity salt response curves of three compositions comprising lauryl lactyllactate made from (1) L-lactide or (2) a 15:85 mixture of L-lactide and meso-lactide or (3) racemic lactide

Viscosity salt responses of the three compositions were tested according to the viscosity salt response test method as describe above, and the results are shown in FIG. 22. The results show that L3 using L-lactide has a better viscosity building property than L3 using L/meso lactide, which in turn is better than L3 using racemic lactide.

Example 39

Comparative Study of the Lactic Acid Process of U.S. Pat. No. 3,144,341 and the Lactic Acid Process of the Present Technology The lactic acid method of U.S. Pat. No. 3,144,341 (the '341 patent) was reproduced in this example, and was compared to the lactic acid method of the present technology. According to the description of the '341 patent, no catalyst was used, and the equivalent molar ratio of lactic acid to lauryl alcohol was about 2.1:1. Six experiments (Experiments 1-6) of the lactic acid method of the present technology were conducted in a process similar to that described in Example 35 above. In each of the Experiments 1-5, NAFION, pTSA, methanesulfonic acid, $BF_3$ etherate, or phosphoric acid was used as the catalyst, and the lactic acid and lauryl alcohol were used in an equivalent molar ratio of about 4:1. Experiment 6 used pTSA as the catalyst, and the lactic acid and lauryl alcohol were used in an equivalent molar ratio of about 8:1. The L2 to L3 ratio of each reaction product obtained by GC analysis was shown in Table 25 below.

TABLE 25

| Process | Lauryl alcohol Equivalent | Lactic Acid Equivalents | Catalyst | Ratio of L2:L3 |
|---|---|---|---|---|
| U.S. Pat. No. 3,144,341 | 1 | 2.1 | None | 2.3:1 |
| Experiment 1 | 1 | 4 | NAFION | 1.2:1 |
| Experiment 2 | 1 | 4 | pTSA | 0.9:1 |
| Experiment 3 | 1 | 4 | Methanesulfonic acid | 1.1:1 |
| Experiment 4 | 1 | 4 | $BF_3$ etherate | 1:1 |
| Experiment 5 | 1 | 4 | Phosphoric acid | 1.3:1 |
| Experiment 6 | 1 | 8 | pTSA | 0.7:1 |

The results showed that the lactic acid method of the present technology can provide a product containing a much higher ratio of L3 to L2 as compared to the product obtained by the method of the '341 patent.

The present technology is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the present technology as set forth in the appended claims.

We claim:
1. A composition comprising:
an alkyl lactyllactate reaction product comprising at least 50% by weight of at least one alkyl lactyllactate of the following general structure:

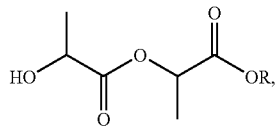

wherein R is an alkyl group or alkoxylated alkyl group; at least one surfactant; and water.

2. The composition of claim 1, wherein the composition exhibits a reduction in critical micelle concentration of from about 5% to about 99% as compared to a comparative surfactant composition comprising said at least one surfactant without alkyl lactyllactate, wherein the total weight concentrations of surfactant actives in said composition and in said comparative surfactant composition are substantially the same.

3. The composition of claim 2, wherein the composition exhibits a reduction in critical micelle concentration of at least about 15%.

4. The composition of claim 1, wherein R comprises an alkyl group of from about 6 to about 22 carbon atoms.

5. The composition of claim 4, wherein R further comprises from about 1 to about 12 moles of an alkoxylate of about two to about six carbon atoms per mole of the alkyl lactyllactate.

6. The composition of claim 5, wherein the alkoxylate is ethoxylate or propoxylate or a mixture thereof.

7. The composition of claim 1, wherein the at least one alkyl lactyllactate is an L-lactyllactate, a rac-lactyllactate made from meso-lactide, or a mixture of L-lactide and meso-lactide.

8. The composition of claim 7, wherein the mixture comprises about 15% to about 70% L-lactide, based on the total weight of the mixture.

9. The composition of claim 1, wherein the at least one alkyl lactyllactate is lauryl lactyllactate.

10. The composition of claim 1, wherein the alkyl lactyllactate reaction product is the reaction product of lactic acid reacted with at least one hydroxyl containing compound.

11. The composition of claim 10, wherein the lactic acid is L-lactic acid.

12. The composition of claim 10, further comprising at least one alkyl lactate produced during the reaction of the lactic acid and the at least one hydroxyl containing compound.

13. The composition of claim 1, wherein the at least one surfactant comprises at least one salt of alkyl sulfate, an alkyl alkoxy sulfate, an alkyl alkoxy carboxylate, an alkyl phosphate, an alkyl alkoxy phosphate, an alkyl sulfonate, a sulfonated alkyl methyl or ethyl ester, a sulfonated fatty acid, an alkyl sulfo acetate, an alkyl benzene sulfonate, an alpha olefin sulfonate, a paraffin sulfonate, an alkyl isethionate, an acyl lactylate, a sulfosuccinate, an amphoacetate, a sarcosinate, a poly decyl glucoside carboxylate, a lauryl glucose carboxylate, alkyl glutamate, a fatty acid amide, an ethoxylated fatty acid amide, a fatty alcohol, an alkyl alcohol ethoxylate, an alkyl phenol ethoxylate, a propylene glycol esters, a poly glycerol esters, an ethylene glycol esters, an ethoxylated glycol esters, a polypropylene glycol esters, an alkyl glucoside, an alkylpolyglycoside, an alkyl glucamide, a sorbitan esters, a betaines, an amine oxides, a sultaine, an alkyl trimethylammonium halogenide, a dialkyl dimethyl halogenide, a trialkyl methyl ammonium a halogenide, a polyquaternium, a quaternized cellulose, a quaternized guar gum, an esterquat, an amidoamine quat, an alkyl amidopropyl dimethyl amine quat, a derivative thereof, or a combination thereof.

14. The composition of claim 1, wherein the composition exhibits a reduction in the area per molecule of from about 2% to about 80% as compared to a comparative surfactant composition comprising said at least one surfactant without alkyl lactyllactate, wherein the total weight concentrations of surfactant actives in said composition and in said comparative surfactant composition are substantially the same.

15. The composition of claim 14, wherein the composition exhibits a reduction in the area per molecule of from about 5% to about 60%.

* * * * *